United States Patent
Mulvey et al.

(10) Patent No.: US 10,232,003 B2
(45) Date of Patent: Mar. 19, 2019

(54) EXOGENOUS TAP INHIBITOR ARMED ONCOLYTIC VIRUSES AND THERAPEUTIC USES THEREOF

(71) Applicant: BeneVir Biopharm, Inc., Gaithersburg, MD (US)

(72) Inventors: Matthew Mulvey, North Bethesda, MD (US); Steven Fuhrmann, Germantown, MD (US); Ram Aiyar, Rockville, MD (US)

(73) Assignee: BeneVir Biopharm, Inc., Gaithersburg, MD (US)

( * ) Notice: Subject to any disclaimer, the term of this patent is extended or adjusted under 35 U.S.C. 154(b) by 1 day.

(21) Appl. No.: 15/129,916

(22) PCT Filed: Mar. 30, 2015

(86) PCT No.: PCT/US2015/023268
§ 371 (c)(1),
(2) Date: Sep. 28, 2016

(87) PCT Pub. No.: WO2015/153417
PCT Pub. Date: Oct. 8, 2015

(65) Prior Publication Data
US 2017/0173092 A1    Jun. 22, 2017

Related U.S. Application Data

(60) Provisional application No. 61/972,327, filed on Mar. 30, 2014.

(51) Int. Cl.
*A61K 35/768* (2015.01)
*A61K 35/761* (2015.01)
*A61K 35/766* (2015.01)

(52) U.S. Cl.
CPC .......... *A61K 35/768* (2013.01); *A61K 35/761* (2013.01); *A61K 35/766* (2013.01); *A61K 2121/00* (2013.01); *C12N 2710/10332* (2013.01); *C12N 2710/16033* (2013.01); *C12N 2710/24132* (2013.01); *C12N 2760/20232* (2013.01)

(58) Field of Classification Search
CPC ...... A61K 2039/5256; A61K 2039/572; A61K 2039/585; A61K 15/86; C12N 2710/16632
See application file for complete search history.

(56) References Cited

U.S. PATENT DOCUMENTS

| | | | |
|---|---|---|---|
| 5,750,398 | A | 5/1998 | Johnson et al. |
| 5,843,458 | A | 12/1998 | Jones et al. |
| 5,858,376 | A | 1/1999 | Johnson et al. |
| 5,908,780 | A | 6/1999 | Jones et al. |
| 6,033,671 | A | 3/2000 | Frueh et al. |
| 7,510,868 | B2 | 3/2009 | Harden et al. |
| 8,158,599 | B2 | 4/2012 | Harden et al. |
| 2006/0039894 | A1 | 2/2006 | Mohr et al. |
| 2007/0264282 | A1 | 11/2007 | Coffin |
| 2010/0092435 | A1 | 4/2010 | Wiertz et al. |
| 2011/0070262 | A1 | 3/2011 | Johnson et al. |
| 2013/0136768 | A1 | 5/2013 | Frueh et al. |
| 2013/0142823 | A1 | 6/2013 | Frueh et al. |
| 2013/0280283 | A1 | 10/2013 | Lorenz et al. |

FOREIGN PATENT DOCUMENTS

| | | |
|---|---|---|
| EP | 1599780 A1 | 11/2005 |
| WO | 9825645 A1 | 6/1998 |
| WO | 2009008713 A1 | 1/2009 |
| WO | 2008069663 A1 | 6/2012 |
| WO | 2013036795 A3 | 5/2014 |

OTHER PUBLICATIONS

Liu et al., "ICP 34.5 Deleted Herpes Simplex Virus with Enhanced Oncolytic, Immune Stimulating, and Anti-Tumour Properties", Gene Therapy, 2003, vol. 10, pp. 292-303.
Mohr et al., "A Herpes Simplex Virus Type 1 g34.5 Second-Site Suppressor Mutant That Exhibits Enhanced Growth in Cultured Glioblastoma Cells Is Severely Attenuated in Animals", Journal of Virolology, Jun. 2001, vol. 75, No. 11, p. 5189-5196.
Dosten et al., "Tap-Inhibiting Proteins US6, ICP47, and UL49.5 Differentially Affect Minor and Major-Histocompatibility Antigen-Specific Recognition by Cytotoxic T Lymphocytes.", International Immunology, Sep. 1, 2007, vol. 19, No. 9, pp. 1115-1122, XP055146741.
Spector et al., Mutational Analysis of the Promoter Region of the a27 Gene of Herpes Simplex Virus 1 Within the Context of the Viral Genome, Proc. Natl. Acad. Sci. USA, 1990, vol. 87, pp. 5268-5272.
International Search Report and Written Opinion from corresponding PCT/US2015/023268, dated Jun. 16, 2015.
Raafat et al., "Preventing Vaccinia Virus Class-I Epitopes Presentation by Hsv-ICP47 Enhances the Immunogenicity of a Tap-Independent Cancer Vaccine Epitope", International Journal of Cancer, vol. 131, No. 5, Jan. 3, 2012, pp. E659-E669, XP055192334.
Wang et al., "Recombinant Adenovirus Expressing ICP47 Gene Suppresses the Ability of Dendritic Cells by Restricting Specific T Cell Responses", Cellular Immunology, vol. 282, No. 2, Apr. 1, 2013, pp. 129-135, XP055192391.
Momburg et al., "Corking the Bottleneck: The Transporter Associated with Antigen Processing as a Target for Immune Subversion by Viruses.", Current Topics in Microbiology and Immunology, vol. 269, 2002, pp. 57-74, XP009184551.
Bartlett et al., "Oncolytic Viruses as Therapeutic Cancer Vaccines", Molecular Cancer, vol. 12, No. 1, Sep. 11, 2013, p. 103, XP021159944.

*Primary Examiner* — Bao Q Li
(74) *Attorney, Agent, or Firm* — Michele M. Wales; Inhouse Patent Counsel, LLC

(57) ABSTRACT

The present invention relates to exogenous TAP inhibitor armed oncolytic viruses that replicate selectively in cancer cells, evade CD8+ cytolytic T-cells, and induce the immune system to recognize tumor cells. Preferred viruses of the invention have a heterologous gene that encodes a function that affects antigen presentation by inhibiting TAP. The viruses of the invention also comprise one or more heterologous genes encoding immunomodulatory polypeptides, prodrug converting enzymes, or matrix degrading enzymes. Compositions and therapeutic methods using the oncolytic viruses are also provided, including compositions and therapeutic methods for treating cancers, such as melanoma, head and neck cancer, ovarian cancer, breast cancer, glioblastoma, bladder cancer, prostate cancer, lung cancer, liver cancer, colorectal cancer, pancreatic cancer, and renal cancer.

23 Claims, 1 Drawing Sheet

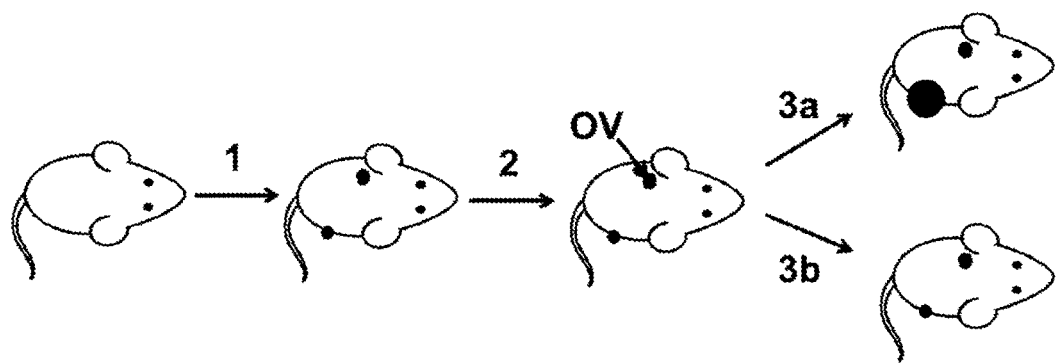

EXOGENOUS TAP INHIBITOR ARMED ONCOLYTIC VIRUSES AND THERAPEUTIC USES THEREOF

CROSS-REFERENCE TO RELATED APPLICATIONS

This application is a § 371 National Stage Application of PCT/US2015/023268, filed Mar. 30, 2015, which claims priority to U.S. Application No. 61/972,327, filed Mar. 30, 2014. All of these documents (PCT/US2015/023268 and U.S. 61/972,327) are hereby incorporated by reference in their entirety.

FIELD OF THE INVENTION

The present invention relates to exogenous TAP inhibitor armed oncolytic viruses that replicate selectively in cancer cells, evade CD8+ cytolytic T-cells, and induce the immune system to recognize tumor cells. Compositions and therapeutic methods using the oncolytic viruses are also provided, including compositions and therapeutic methods for treating cancers, such as melanoma, head and neck cancer, ovarian cancer, breast cancer, glioblastoma, bladder cancer, prostate cancer, lung cancer, liver cancer, colorectal cancer, pancreatic cancer, and renal cancer.

BACKGROUND OF THE INVENTION

While the underlying goal of cancer therapy is to destroy the cancer while avoiding excessive damage to the normal organs of the body, their toxic effects to the body limit present treatments such as chemotherapy and radiation. As such, the maximal tolerable dosage of such therapies is often inadequate to eradicate the tumor. Newer treatment strategies have focused upon identifying antineoplastic agents that can distinguish normal cells from their cancerous counterparts. Oncolytic viruses replicate, spread and selectively destroy cancerous tissue, but are attenuated and do not harm normal tissues. In addition to direct oncolysis, an immune-mediated component contributes to oncolytic virus efficacy in immune-competent mice (i.e., oncolytic viruses have a tumor-vaccination effect mediated at least in part through an anti-tumor CD8+ T cell response). Using immune-competent mice with syngeneic, bilateral subcutaneous (s.c.) tumors, previous studies established that treatment of one tumor with oncolytic virus (HSV-1) induced regression of the treated and untreated contralateral tumor (see Toda M, et al. "Herpes simplex virus as an in situ cancer vaccine for the induction of specific anti-tumor immunity." Hum Gene Ther 1999; 10:385-93). While treated and untreated tumors both regressed, oncolytic virus was only detected in the treated tumor. Furthermore, regression of the uninjected, contralateral tumor resulted from an anti-tumor CD8+ T-cell response.

However, the current forms of oncolytic viruses are severely limited in their use. Viral replication and spread in normal cells is what causes pathogenesis and must be avoided in oncolytic viruses. There are two general ways of ensuring that a virus does not replicate in normal human tissue. The first way is to identify naturally occurring, non-pathogenic viruses, usually from other animals, that do not replicate efficiently in normal human cells. The second way is to make alterations to pathogenic viruses so that they can no longer replicate efficiently in normal human cells, but do replicate in tumor cells.

Identifying naturally occurring non-pathogenic viruses, especially those from other animals, which do not replicate in normal human cells is generally done by isolating viruses from other animals like rodents or birds and testing the ability of these viruses to infect and replicate in normal human cells as well as human tumor cells. This strategy has identified several viruses such as New Castle Disease Virus, Vesicular Stomatitis Virus, Myxoma Virus, and Seneca Valley Virus, among others, which do not replicate well in normal human cells, but exhibit higher levels of replication and cell killing when they infect human tumor cells. Each of these viruses is a pathogen for a specific lower animal and evolution has finely tuned the genes of these viruses for optimal function in the cells of those animals. For a virus to be successful, functions encoded by viral genes must be compatible with the basic molecular circuitry of the host cell so that they can function to direct synthesis of the viral components necessary to manufacture progeny viruses and spread to uninfected cells. Also, to be successful, the virus must fight off attempts by the infected host cell to block viral replication.

The basic molecular circuitry and anti-viral defense mechanisms of mammalian cells are homologous. This means that a virus adapted for replication in, for example, mouse cells, will likely be able to replicate in human cells, albeit with substantially reduced efficiency because, after all, despite the similarities, there are still big differences between mouse and human cells. For the most part, this ensures that viruses from other animals are not pathogenic to humans. However, because of unrestrained cell growth, tumor cells, compared to normal cells, are often not very good at defending themselves against viruses. This is the basis for using naturally occurring viruses from other animals as anti-cancer agents. These viruses are intrinsically compatible with the molecular circuitry of the human cell and are able to infect and replicate relatively freely in tumor cells because the tumor cell is not very good at blocking the viral replicative program compared to normal cells.

At first glance, the idea of using viruses evolved to efficiently infect and replicate in the normal cells of another animal is a good way to ensure tumor specific replication of an oncolytic virus. However, evolution has shaped these viruses to be very good at replicating in nonhuman cells and their replicative ability is still relatively inefficient in human tumor cells compared to viruses that have co-evolved with humans and are optimized for replication in human cells.

While the idea of using a human virus, optimized through evolution for replication in human cells, is an attractive option for cancer treatment, there is great risk associated with treating humans with a human pathogen precisely because evolution has shaped the human virus to be very good at what it does: infect, replicate in, and kill normal human cells. Therefore, much effort has gone into identifying which genes of human viruses are required for directing viral replication in normal cells, but are not required in tumor cells. This strategy seeks to create mutant human viruses deficient in the genes required for replication in normal cells in order to attenuate the virus, but still maintain the ability to infect, replicate in and kill tumor cells. This strategy has resulted in the creation of adenovirus and Herpes Simplex Virus Type 1 (HSV-1) mutants that do not replicate efficiently in normal human cells and replicate better in many types of human tumor cells. Indeed, the most advanced and clinically successful oncolytic viruses to date are mutant versions of adenovirus (H101—Shanghai Sunway Biotech) and HSV-1 (T-Vec—Amgen), the wildtype versions of which are human viral pathogens.

The ability of an oncolytic virus to replicate efficiently in tumor cells is important, but it is not the only factor affecting therapeutic efficacy. One major obstacle to successful cancer treatment using oncolytic viruses is the adaptive immune system, which is very good at containing viruses at the site of infection by limiting viral spread. The adaptive immune system curtails viral spread by manufacturing antibodies that are able to recognize, bind, and inactivate virus particles before they have a chance to bind to the surface of an uninfected cell and initiate a new round of infection. The adaptive immune system also employs anti-viral CD8+ cytolytic T lymphocytes (CTL), which recognize viral peptides displayed on the infected cell surface by MHC-I. When a CD8+ CTL recognizes a viral peptide displayed by MHC-I, it proceeds to kill the cell. Cell surface display of viral peptides on MHC-I is a key mechanism employed by cells to signal to the immune system that they are infected and should be killed before the virus has been able to synthesize progeny, which are necessary for initiating new rounds of infection and facilitating viral spread from one cell to another.

The adaptive immune system, especially CD8+ CTL, are both friend and foe to oncolytic viruses. They are foes for the reason cited above: CD8+ CTL curtail viral spread and eliminate the virus by killing infected cells, which are the factories assembling the virus particles necessary for sustained viral infection. Limited, transient, oncolytic virus infection that is rapidly cleared minimizes the number of tumor cells killed by the virus and limits therapeutic efficacy. Maximizing the number of tumor cells killed by the virus is important because virally killed tumor cells are excellent substrates for professional antigen presenting cells (pAPC). Virally killed tumor cells are thought to provide tumor associated antigens (TAA) to pAPC and viral replicative intermediates such as double stranded RNA (dsRNA) induce maturation of pAPC and expression of co-stimulatory molecules through Toll like receptor signaling. Mature TAA-load pAPC are able to induce activation and expansion of antitumor CD8+ CTL capable of killing tumor cells that display TAA in complex with MHC-I. These anti-tumor CD8+ CTL are major effectors of anti-tumor immunity and the focus of many immunotherapies that seek to induce the immune system to recognize and eliminate tumor cells throughout the body as if cancer were a simple bacterial or viral infection. Thus, from the viewpoint of an oncolytic virus, there are two types of CD8+ CTL: Anti-viral (Foes) and Anti-tumor (Friends).

The pAPC is a lynchpin in the mechanism of anti-tumor immune induction by oncolytic viruses. Tumor resident pAPC are responsible for processing virally killed cells, displaying TAA, and migrating to the tumor draining lymph node (TDLN) where they induce activation and maturation of anti-tumor CD8+ CTL. Anything that interferes with this ability reduces the efficiency at which anti-tumor immunity is induced by oncolytic virus treatment. Many oncolytic viruses, including Vaccinia, adenovirus, and HSV-1 oncolytic viruses have been shown to infect pAPC and induce the cells to kill themselves through apoptosis. From this perspective, oncolytic viruses are their own worst enemy: they kill the messenger responsible for communicating tumor information to anti-tumor CD8+ CTL.

Thus, there is a strong need to develop new oncolytic viruses that are both safe for the patient and effectively use the patient's own immune system to eliminate tumor cells. In other words, one approach to improving oncolytic viruses is to maximize their ability to spread through tumor tissue in order to kill as many tumor cells as possible and efficiently stimulate friendly immune responses (anti-tumor) while also minimizing the effect enemy immune responses exert on viral replication and spread (anti-viral).

The antigen presentation system (APS) is the major mechanism cells employ to tell the immune system that they are infected with a virus. Specifically, the APS mediates display of cellular and viral peptides in complex with MHC-I at the cell surface. By displaying viral peptides at the cell surface, the infected cell hoists a distinctive flag that tells CD8+ CTL the cell is infected with a virus. If the CD8+ CTL recognizes the viral peptide-MHC-I complex, it will kill the cell in order to stop the virus from continuing to use the cell to produce progeny viruses. The transporter associated with antigen processing (TAP) protein is responsible for carrying peptides from the cytoplasm into the endoplasmic reticulum (ER). Once inside the endoplasmic reticulum, these peptides are loaded on MHC-I for display at the cell surface. One family of viruses, the Herpesviruses, have uniquely evolved functions to inhibit TAP thereby blocking the display of viral peptides, which prevents CD8+ CTL from recognizing and killing virus infected cells. However, to date, only certain members of the herpesvirus family and only one member outside the herpesvirus family, namely cowpox, have been able to evolve TAP inhibitor functions. This selective pressure against evolution of TAP inhibition outside of the herpes family suggests that virally encoded functions that inhibit TAP must have unintended consequences and therefore have been ameliorated by other viral function in order to allow for the permissive evolution of TAP inhibitor function in the viral genome to be of net benefit to the virus's goal of maintaining itself in the host.

It is well established that inhibition of TAP leads to downregulation of peptide-MHC-I complexes from the cell surface (Oosten L E, et al. "TAP-inhibiting proteins US6, ICP47 and UL49.5 differentially affect minor and major histocompatibility antigen-specific recognition by cytotoxic T lymphocytes." Int Immunol 2007; 19(9): 1115-22). NK cells are known to kill cells that are defective in TAP activity and exhibit low levels of peptide-MHC-I complexes at the cell surface (reviewed in Cassidy S A, et al. "Effects of peptide on NK cell-mediated MHC I recognition." Front Immunol 2014; 1-8). Clearly, NK cells have the ability to identify cells infected with a virus that encodes a TAP inhibitor. Indeed, a seminal study examined an adenovirus gene therapy vector administered to rhesus macaques. The vector directed expression of the human cystic fibrosis transmembrane regulator (hCFTR) after instillation into the lungs. In addition, it expressed the HSV-1 TAP inhibitor ICP47 with the hope that TAP inhibition would improve the longevity of hCFTR expression by precluding elimination of virally transduced cells by CD8+ CTL that recognize adenoviral antigens displayed by MHC-I. While cells transduced by the vector were resistant to killing by CD8+ CTL, the cells exhibited increased sensitivity to killing by NK cells resulting in no clear improvement in the long term expression of the hCFTR mRNA in transduced rhesus macaque lung tissue (Scaria A., et al. "Adenoviral vector expressing ICP47 inhibits adenovirus-specific cytotoxic T lymphocytes in nonhuman primates." Mol Ther 2000; 2(5): 505-14). Therefore, any virus encoding a TAP inhibitor must also have a way of dealing with the negative consequences of TAP inhibition, namely by enabling the infected cell to be hidden from killing by NK cells. Therefore, while inserting a TAP inhibitor into a virus that does not naturally encode a TAP inhibitor may be successful in facilitating viral evasion of CD8+ CTL, it may result in increased killing by NK cells and thus have no ultimate benefit to the virus. This may be why so few viral pathogens, outside the herpes family, have found TAP inhibitors useful.

Due to the complex nature of viral genetic networks and the multiple mechanisms the immune system employs to identify and kill virally infected cells, there is no clear consensus as to how to modify oncolytic viruses to mitigate the negative aspects the immune system exerts on oncolytic viruses while simultaneously maximizing the positive effects the immune system exerts on behalf of oncolytic viruses in the killing of uninfected tumor cells.

SUMMARY OF THE INVENTION

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject.

The present invention relates to exogenous TAP inhibitor armed oncolytic viruses that are vectors comprising a heterologous polynucleotide encoding a TAP inhibitor, which can be used in the treatment of cancer. In a preferred embodiment, the exogenous TAP inhibitor armed oncolytic virus further comprises an immunomodulatory polypeptide, a prodrug converting enzyme, and/or a matrix degrading enzyme.

The exogenous TAP inhibitor armed oncolytic virus of the present invention can also comprise a promoter. Examples of suitable promoters are well within the art. Examples of such promoters include the CMV promoter, the EFla promoter, and viral and host cell promoters.

Additionally, pharmaceutical formulations comprising an exogenous TAP inhibitor armed oncolytic virus and a pharmaceutically acceptable carrier for administration to tumor cells are provided herein.

The present invention also comprises a method of treatment of a patient with cancer with an exogenous TAP inhibitor armed oncolytic virus. In a preferred embodiment, the patient with cancer has melanoma, head and neck cancer, ovarian, glioblastoma, bladder, breast cancer, lung cancer, renal cell cancer, colorectal cancer, prostate cancer, or pancreatic cancer.

In preferred embodiments, the exogenous TAP inhibitor armed oncolytic virus is used to kill tumor cells in a subject comprising: administering to a subject in need thereof a pharmaceutical formulation described above under conditions effective to kill tumor cells in the subject is also provided. Non-limiting examples of tumor cells that can be killed according to the methods described herein, include, e.g., astrocytoma, oligodendroglioma, meningioma, neurofibroma, glioblastoma, ependymoma, schwannoma, neurofibrosarcoma, medulloblastoma, melanoma cells, pancreatic cancer cells, prostate carcinoma cells, breast cancer cells, lung cancer cells, colon cancer cells, hepatoma cells, mesothelioma, bladder cancer cells, ovarian cancer cells, renal cancer cells, and/or epidermoid carcinoma cells. In certain embodiments, the exogenous TAP inhibitor armed oncolytic virus can selectively replicate in human cancer cells. Administration to a subject can be carried out by injection, infusion, instillation or inhalation. In any of the above embodiments, a subject can be a mammal, such as a human.

In one embodiment, a method for treating cancer is also provided, wherein the method comprises administering to an individual in need of treatment, a therapeutically effective amount of a pharmaceutical formulation described above. In certain embodiments, the cancer is selected from the group consisting of bladder cancer, melanoma, ovarian cancer, glioblastoma, astrocytoma, oligodendroglioma, meningioma, neurofibroma, glioblastoma, ependymoma, Schwannoma, neurofibrosarcoma, medulloblastoma, melanoma cells, pancreatic cancer cells, prostate carcinoma cells, breast cancer cells, lung cancer cells, colon cancer cells, hepatoma cells, mesothelioma, bladder cancer cells, ovarian cancer cells, renal cancer cells, and/or epidermoid carcinoma cells.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 1 shows a bilateral tumor model described in Example 5.

DETAILED DESCRIPTION

The details of one or more embodiments of the invention are set forth in the accompanying drawings and the description below. Other features, objects, and advantages of the invention will be apparent from the description and drawings, and from the claims.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to "a polypeptide" includes a mixture of two or more such polypeptide molecules or a plurality of such polypeptide molecules. Similarly, reference to a "polynucleotide" includes a mixture of two or more such polynucleotide molecules or a plurality of such polynucleotide molecules.

As used herein, the term "comprise" or variations thereof such as "comprises" or "comprising" are to be read to indicate the inclusion of any recited integer (e.g., a feature, element, characteristic, property, method/process step or limitation) or group of integers (e.g., features, element, characteristics, properties, method/process steps or limitations) but not the exclusion of any other integer or group of integers. Thus, as used herein, the term "comprising" is inclusive and does not exclude additional, unrecited integers or method/process steps.

In embodiments of any of the compositions and methods provided herein, "comprising" may be replaced with "consisting essentially of" or "consisting of". The phrase "consisting essentially of" is used herein to require the specified integer(s) or steps as well as those which do not materially affect the character or function of the claimed invention. As used herein, the term "consisting" is used to indicate the presence of the recited integer (e.g., a feature, element, characteristic, property, method/process step or limitation)

or group of integers (e.g. features, element, characteristics, properties, method/process steps or limitations) alone.

The invention will be described in more detail below.

Definitions

The present invention provides novel exogenous TAP inhibitor armed oncolytic viruses with improved anti-tumor activity and improved ability to evade host immune responses. In particular, the exogenous TAP inhibitor armed oncolytic virus provided herein are attenuated, replicate in and destroy neoplastic cells, have improved activity in syngeneic, immune-competent murine models, and/or can be used to treat multiple types of human cancers.

In the present invention, "an exogenous TAP inhibitor armed oncolytic virus" is defined as a virus (viral backbone) that in its natural, wildtype, form does not have an endogenous polynucleotide sequence that encodes for a TAP inhibitor and has been genetically modified to comprise a polynucleotide sequence encoding an exogenous TAP inhibitor. Examples of such viruses that do not have endogenous polynucleotide sequences that encode for a TAP inhibitor include but are not limited to vaccinia virus, adenovirus, adeno-associated virus (AAV) viral vectors, myxoma virus, vesicular stomatitis virus, New Castle Disease Virus, Seneca Valley Virus, and/or reovirus. Preferred examples of vaccinia virus include, but are not limited to members of the following strains Wyeth, Lister, Temple of Heaven, Patwadanger, and/or Modified Vaccinia Virus Ankara. Preferred examples of adenovirus include, but are not limited to, Adenovirus serotypes 5, 2, and 3.

The term "exogenous" refers to a combination of elements not naturally occurring. Thus, for example, an "exogenous TAP inhibitor" refers to a TAP inhibitor to be introduced to the genome of a virus, wherein that gene is not normally found in the virus' genome or is a homolog of a gene expressed in the virus from a different species (e.g., the bovine herpes virus UL49.5 gene, which encodes for a TAP-inhibitor, is exogenous when inserted into the virus genome that does not have a gene that encodes for a TAP-inhibitor.)

In the present invention, a "TAP inhibitor" is defined as a polynucleotide encoding a polypeptide that inhibits either TAP1 (Accession No. CAA47025) or TAP2 (Accession No. CAA47027), or both. Examples of preferred TAP inhibitors include UL49.5 polypeptide from bovine herpesvirus, CMV US6, HSV Us12/ICP47, and/or EBV BNLF2a invention.

Non-limiting examples of UL49.5 include, but are not limited to bovine herpesvirus (BHV), which is capable of inhibiting mouse and human TAP (van Hall et al., J. Immunology (2007) 178:657-662). UL49.5 polypeptides can also be derived from pseudorabies virus (PRV) and equine herpesvirus 1 and 4 (EHV-1 and EHV-4). These UL49.5 proteins interfere with MHC class I antigen presentation by blocking the supply of antigenic peptides through inhibition of TAP and are active on rodent TAP, such as murine TAP. Other examples of TAP inhibitors include UL49.5 polypeptides from bubaline herpesvirus 1 (BuHV-1), cervid herpesvirus 1 (CvHV-1), felid herpesvirus 1 (FeHV-1), (see, Verweij et al., 2011 "Structural and functional analysis of the TAP-inhibiting UL49.5 proteins of varicelloviruses." Mol Immunol. Jul 15 Epub) and BNLF2a and ICP47. It is noted that UL49.5 functional homolog ICP47 from HSV-1 and HSV-2 does not inhibit rodent TAP [see, Koppers-Lalic, D. et al., (2008) PLoS; 4(5): el 000080].

| TAP Inhibitor | Virus |
| --- | --- |
| ICP47 | Herpes Simplex Virus Types 1 and 2 (HSV1/2) |
| UL49.5 | Bovine Herpes Virus-1 (BHV-1) |
| UL49.5 | Bubaline Herpes Virus Type 1(BuHV-1) |
| UL49.5 | Cervid Herpes Virus Type-1 (CvHV-1) |
| UL49.5 | Feline Herpes Virus Type 1 (FeHV-1) |
| UL49.5 | Equine Herpes Virus Types 1 and 4 (EHV-1/4) |
| UL49.5 | Pseodrabies Virus (PRV) |
| Us6 | Human Cytomegalovirus (HCMV) |
| BNLF2α | Epstein Barr Virus (EBV) |
| CPXV12 | Cowpox Virus (CPXV) |

However, it is specifically contemplated that the TAP inhibitor of the present invention is not necessarily limited to polypeptides corresponding to the UL49.5 gene. As used herein, the polypeptide will be considered a "TAP inhibitor" according to the present invention based on a polypeptide's "TAP inhibitor activity" as determined by measuring the ability of the polypeptide to inhibit TAP-dependent transport, facilitated by either TAP1 or TAP2, of peptides into the endoplasmic reticulum of a cell. Assays measuring TAP activity are well known in the art and include, but are not limited to those assays described herein, and in particular as detailed in the Examples and/or the section entitled "Assays Measuring TAP activity."

The exogenous TAP inhibitor armed oncolytic virus of the present invention may additionally comprise a polynucleotide that encodes an "immunomodulatory polypeptide." As used herein, an "immunomodulatory polypeptide" includes immunostimulatory polypeptides, such as, but not limited to, IL-12, GM-CSF, TNF-α, CD40L, IL-10, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, G-CSF, IFN-α, IFN-β, IFN-γ, IL-20 (MDA-7), or a co-stimulatory molecules, such as B7-1 (CD80) and B7-2 (CD86), or an immune checkpoint blocker such as polypeptides that block signaling through PD-1, CTLA-4 or PDL-1. Those exemplary polypeptides recruit and/or activate immune cells to infiltrate tumors, process immunoactive molecules, recognize tumor cells and/or lyse tumor cells (e.g., help mediate the oncolytic function of the exogenous TAP inhibitor armed oncolytic virus of the invention), and, therefore, up-modulate the host immune response. Importantly, in certain embodiments, the presence of immunostimulatory polypeptides, e.g., GM-CSF, which can enhance immune recruitment to virally infected cells and tumors, has the potential to be deleterious to viral infection of tumor cells and viral spread throughout tumor tissue. Thus, it is particularly preferred that the exogenous TAP inhibitor armed oncolytic virus of the invention additionally comprise a heterologous polypeptide that is capable of enhancing the immune evasion capabilities, and therefore the replication and spread, of the exogenous TAP inhibitor armed oncolytic virus, such as, but not limited to polypeptides that inhibit viral antigen presentation by infected cells. In a preferred embodiment, the "immunomodulatory polypeptide" is defined as any one of the following molecules: a granulocyte macrophage colony-stimulating factor (GM-CSF), tumor necrosis factor (TNF)-alpha, CD40 ligand (CD40L), IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, G-CSF, IFN-α, IFN-β, IFN-γ, IL-20 (MDA-7), or a co-stimulatory molecules, such as B7-1 (CD80) and B7-2 (CD86), or an immune checkpoint blocker such as polypeptides that block signaling through PD-1, CTLA-4 or PDL-1.

The immunomodulatory gene may be any gene encoding a polypeptide that is capable of modulating an immune response. The polypeptide capable of modulating an immune response may be a polypeptide capable of inhibiting antigen presentation on class I MHC molecules, or a class I MHC molecule maturation inhibitor (e.g., murine CMV mK3, human CMV US2 and US 11 (not related to HSV Us 11), and varicella zoster virus ORF66). The polypeptide capable of modulating an immune response also may be a cytokine such as, but not limited to, GM-CSF, TNF-a, an interleukin (for example IL12), an interferon (such as IFNy), a chemokine such as RANTES or a macrophage inflammatory protein (MIP) (for example, MIP-3), or another immunomodulatory molecule such as B7.1 (CD80), B7.2 (CD86) or CD40L.

The exogenous TAP inhibitor armed oncolytic virus of the present invention may additionally comprise a polynucleotide that encodes a "prodrug converting enzyme" which is defined as an enzyme that converts a molecule with less activity against a target into a molecule with more activity against a target, for example a cytosine deaminase. A prodrug activating polypeptide can be a cytosine deaminase enzyme, which is capable of converting the inactive prodrug 5-fluorocytosine to the active drug 5-flurouracil. Various cytosine deaminase genes are available including those of bacterial origin and of yeast origin. A second gene, typically a gene encoding a second enzyme, may be used to enhance the prodrug conversion activity of the cytosine deaminase gene. For example, the second gene may encode a uracil phosphoribosyltransferase. Another example of a prodrug converting enzyme is the HSV-1 thymidine kinase.

The exogenous TAP inhibitor armed oncolytic virus of the present invention may additionally comprise a polynucleotide that encodes a "matrix degrading enzyme" which is defined in the present invention as an enzyme that degrades or modifies extra-cellular matrix components in order to facilitate viral spread through the tumor, for example, a matrix metalloproteinase. Non-limiting examples of matrix degrading enzymes are: matrix metalloproteinases such as collagenases, gelatinases and stromelysins, relaxin, bacterial collagenase and chondroitinase ABC I.

The exogenous TAP inhibitor armed oncolytic virus of the present invention may additionally comprise a polynucleotide that encodes a "fusogenic gene" which is defined in the present invention as a gene encoding a polypeptide capable of causing cell to cell fusion may be used. Preferably the polypeptide capable of causing cell to cell fusion is selected from a modified retroviral envelope glycoprotein, such as an envelope glycoprotein derived from gibbon ape leukemia virus (GALV) or human endogenous retrovirus W, a fusogenic F or H protein from measles virus and the vesicular stomatitis virus G protein. More preferably, the polypeptide capable of causing cell to cell fusion is a GALV fusogenic glycoprotein (see, Simpson et al. (2006) "Combination of a Fusogenic Glycoprotein, Prodrug Activation, and Oncolytic Herpes Simplex Virus for Enhanced Local Tumor Control." Cancer Res; 66:9: 4835-4842).

The polypeptide capable of causing cell to cell fusion may also be capable of modulating an immune response. For example, GALV is capable of modulating an immune response. The exogenous TAP inhibitor armed oncolytic virus of the invention may thus be used to deliver the genes to a cell in vivo where they will be expressed.

It is specifically contemplated that functional variants of any of the recited immunomodulatory proteins, prodrug converting enzymes, matrix degrading enzymes, and/or fusogenic proteins can also be included in the exogenous TAP inhibitor armed oncolytic virus described herein. For example, variants of at least 70%, of at least 80% of at least 90%, of at least 95%, of at least 96%, of at least 97%, of at least 98%, and/or of at least 99% of any of the immunomodulatory proteins, prodrug converting enzymes, matrix degrading enzymes, and/or fusogenic proteins recited herein can be included in the exogenous TAP inhibitor armed oncolytic virus described herein.

In preferred embodiments, the exogenous TAP inhibitor armed oncolytic virus comprises: a polynucleotide cassette comprising: at least two heterologous genes encoding a polypeptide capable of enhancing an anti-tumor response, and a pharmaceutically acceptable carrier for administration to tumor cells.

In a particularly preferred embodiment, the exogenous TAP inhibitor armed oncolytic virus of the invention has a polynucleotide cassette comprising: a gene encoding a mammalian IL-12 gene, and a gene encoding a TAP inhibitor.

Although the invention is not limited by any particular theory or mechanism of action, the ability of the virus to inhibit TAP increases its ability to evade host immune responses (e.g., cytolytic CD8 T-cell responses), thereby improving the ability of the virus to spread throughout and kill tumor cells before being cleared by the host immune response. Furthermore, in certain embodiments, the exogenous TAP inhibitor armed oncolytic virus of the invention is particularly useful in animal models, e.g., rodent models of cancer, because they comprise a gene encoding a TAP inhibitor active on murine TAP.

Preferably, the exogenous TAP inhibitor armed oncolytic virus comprises: a polynucleotide cassette comprising: at least two, at least three, at least four, and/or at least five different genes encoding a polypeptide capable of enhancing an anti-tumor response. The exogenous TAP inhibitor armed oncolytic virus of the present invention can also be formulated in a pharmaceutically acceptable carrier for administration to tumor cells.

The terms "polynucleotide cassette" and "gene expression cassette" means a manipulatable fragment of DNA carrying, and capable of expressing, one or more genes of interest between one or more sets of restriction sites. It can be transferred from one DNA sequence (usually on a vector) to another by 'cutting' the fragment out using restriction enzymes and "pasting" it back into the new context. Typically, the DNA fragment (nucleic acid sequence) is operatively associated with expression control sequence elements which provide for the proper transcription and translation of the target nucleic acid sequence(s) (genes). Such sequence elements may include a promoter and a polyadenylation signal. The "polynucleotide cassette" may further comprise "vector sequences". By "vector sequences" is meant any of several nucleic acid sequences established in the art which have utility in the recombinant DNA technologies of the invention to facilitate the cloning and propagation of the polynucleotide cassette including (but not limited to) plasmids, cosmids, bacterial artificial chromosomes, phage vectors, viral vectors, and yeast artificial chromosomes.

The exogenous TAP inhibitor armed oncolytic virus of the invention can infect and replicate in tumor cells. Thus, such viruses are replication competent. Preferably, they are selectively replication competent, i.e., "selectively replicate" in tumor cells. This means that either they replicate in tumor cells and not in non-tumor cells, or that they replicate more effectively in tumor cells than in non-tumor cells. For example, where the exogenous TAP inhibitor armed oncolytic virus is used for treating a tumor, the exogenous TAP inhibitor armed oncolytic virus is capable of replicating more effectively in the tumor cells but less effectively in the surrounding tissue. Cells in which the virus is able to replicate effectively are permissive cells. Measurement of selective replication competence can be carried out by the tests described herein for measurement of replication and tumor cell-killing capacity, and also analyzed by the statistical techniques mentioned herein if desired.

The phrase "enhancing an anti-tumor response" in the context of a exogenous TAP inhibitor armed oncolytic virus means that the "anti-tumor" response induced following infection with a exogenous TAP inhibitor armed oncolytic virus, as measured, for example, and without limitation, by decreased tumor growth, decreased frequency of or size of tumor metastases, increased tumor cell death, increased immune cell tumor infiltration, increased immune cell-mediated tumor cell killing, increased IFN-γ secretion by immune cells in the presence of living, apoptotic or dead tumor cells, increased levels of anti-tumor immune cells in the animal or human, and/or increased induction of anti-tumor immunity. By way of example, and without limitation, an anti-tumor response is enhanced by a exogenous TAP inhibitor armed oncolytic virus if the exogenous TAP inhibitor armed oncolytic virus increases reduces tumor size by, e.g., at least 1-fold, at least 2-fold, at least 3-fold, at least 4-fold, at least 5-fold, at least 10-fold, at least 20-fold, at least 30-fold, at least 40-fold, at least 50-fold, at least 100-fold, at least 200-fold, at least 500-fold, at least 1000-fold or more, compared to a control virus that does not encode a TAP inhibitor or other inhibitor of antigen presentation.

The terms "express" and "expression" mean allowing or causing the information in a gene or DNA sequence to become manifest, for example producing a polypeptide encoded by the gene or DNA sequence. As used herein, a gene or DNA sequence is expressed in or by a virus to form an "expression product" such as a polypeptide. The expression product itself, e.g., the resulting polypeptide, may also be said to be "expressed" by the virus.

The term "gene", also called a "structural gene" means a DNA sequence that codes for or corresponds to a particular sequence of amino acids which comprise all or part of one or more polypeptides (e.g., proteins), and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" expression control sequences in a virus or cell when RNA polymerase transcribes the coding sequence into RNA, particularly mRNA, which is then spliced (if it contains introns) and translated into the polypeptide encoded by the coding sequence.

The term "expression control sequence" refers to a promoter and any enhancer or suppression elements that combine to regulate the transcription of a coding sequence. In a preferred embodiment, the element is a transcriptional promoter.

A sequence "encoding" an expression product, such as a polypeptide, is a minimum nucleotide sequence that, when expressed, results in the production of that polypeptide.

The term "host cell" means any cell of any organism that is selected, modified, transformed, grown, infected or used or manipulated in any way for the production of a substance by the cell or to grow, test, screen, or carry out another desired activity on, a exogenous TAP inhibitor armed oncolytic virus of the invention. For example, a host cell may be one that is manipulated to express a particular gene, a DNA or RNA sequence, a polypeptide. In a preferred embodiment, a host cell is any one which is capable of being infected with an exogenous TAP inhibitor armed oncolytic virus of the invention, e.g., for screening or other assays that are described infra, e.g., for screening the activity, replication and protein synthesis efficiency of the exogenous TAP inhibitor armed oncolytic virus of the invention. Such suitable cells are well known in the art. Host cells may be cultured in vitro or one or more cells in a non-human animal (e.g., a transgenic animal or a transiently transfected animal). Exemplary suitable host cells include, but are not limited to, UMUC3, T24, J82 and EJ (MGH-U1), J82 (CO), RT4, RT1 12, TCCSuP and SCaBER cells.

"Treating" or "treatment" of a state, disorder or condition includes: (1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms.

For example, in relation to cancer, the term "treat" may mean to relieve or alleviate at least one symptom selected from the group consisting of tumor growth, metastasis, sensitivity of tumor cells to treatments such as chemotherapy, radiation therapy, thermotherapy, etc. The term "treat" also denotes to arrest, delay the onset (i.e., the period prior to clinical manifestation of a disease) and/or reduce the risk of developing or worsening a disease. In a specific embodiment, treating cancer comprises killing a tumor cell, e.g., with an oncolytic virus of the invention. The benefit to a subject to be treated is either statistically significant or at least perceptible to the patient or to the physician.

"Patient" or "subject" refers to mammals, for example and without limitation, humans, primates, rodents (e.g., mice and rats), dogs, cats, cows, sheep, and veterinary subjects.

An "effective amount" of a compound of the present invention includes doses that partially or completely achieve the desired therapeutic, prophylactic, and/or biological effect. The actual amount effective for a particular application depends on the condition being treated and the route of administration. The effective amount for use in humans can be determined from animal models.

As used herein the term "therapeutically effective" applied to dose or amount refers to that quantity of a compound or composition (e.g., pharmaceutical composition) that is sufficient to result in a desired activity upon administration to an animal in need thereof. Thus, within the context of the present invention, the term "therapeutically effective amount" refers to that quantity of a compound or composition that is sufficient to treat at least one symptom of a cancer, such as but not limited to cancer cell proliferation, tumor growth, resistance to apoptosis, and angiogenesis, and/or to inhibit metastasis of a cancer cell. When a combination of active ingredients is administered, an effective amount of the combination may or may not include amounts of each ingredient that would have been effective if administered individually. A "prophylactically effective amount" is an amount of a pharmaceutical composition that, when administered to a subject, will have the intended prophylactic effect, for example, preventing or delaying the onset (or recurrence) of cancer, or reducing the likelihood of the onset (or recurrence) of cancer or cancer symptoms. The full prophylactic effect does not necessarily occur by administration of one dose, and may occur only after administration of a series of doses. Thus, a prophylactically effective amount may be administered in one or more administrations.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5 fold, and more preferably within 2 fold, of a value. Unless otherwise stated, the term 'about' means within an acceptable error range for the particular value, such as ±1-20%, preferably ±1-10% and more preferably ±1-5%.

As used herein, the terms "mutant" and "mutation" refer to any detectable change in genetic material (e.g., DNA) or any process, mechanism, or result of such a change. This includes gene mutations, in which the structure (e.g., DNA sequence) of a gene is altered, any gene or DNA arising from any mutation process, and any expression product (e.g., polypeptide) expressed by a modified gene or DNA sequence. As used herein, the term "mutating" refers to a process of creating a mutant or mutation.

The term "nucleic acid hybridization" refers to antiparallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an antiparallel hybrid). See Molecular Biology of the Cell, Alberts et al, 3rd ed., New York and London: Garland Publ, 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M NaHPO4, 7% SDS, 1 mM EDTA at 65° C., followed by washing in 0.1×SSC/0.1% SDS at 68° C. (where 1×SSC is 0.15M NaCl, 0.15M Na citrate) or for oligonucleotide molecules washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)). Accordingly, the term "high stringency hybridization" refers to a combination of solvent and temperature where two strands will pair to form a "hybrid" helix only if their nucleotide sequences are almost perfectly complementary (see Molecular Biology of the Cell, Alberts et al, 3rd ed., New York and London: Garland Publ, 1994, Ch. 7).

Conditions of intermediate or moderate stringency (such as, for example, an aqueous solution of 2×SSC at 65° C.; alternatively, for example, hybridization to filter-bound DNA in 0.5 M NaHP04, 7% SDS, 1 mM EDTA at 65° C., and washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA and length and base composition of the probe, and are normally determined empirically in preliminary experiments, which are routine (see Southern, J. Mol. Biol. 1975; 98: 503; Sambrook et al., Molecular Cloning: A Laboratory Manual, 2nd ed., vol. 2, ch. 9.50, CSH Laboratory Press, 1989; Ausubel et al., (eds.), 1989, Current Protocols in Molecular Biology, Vol. I, Green Publishing Associates, Inc., and John Wiley & Sons, Inc., New York, at p. 2.10.3).

As used herein, the term "standard hybridization conditions" refers to hybridization conditions that allow hybridization of sequences having at least 75% sequence identity. According to a specific embodiment, hybridization conditions of higher stringency may be used to allow hybridization of only sequences having at least 80% sequence identity, at least 90% sequence identity, at least 95% sequence identity, or at least 99% sequence identity.

Nucleic acid molecules that "hybridize" to any desired nucleic acids of the present invention may be of any length. In one embodiment, such nucleic acid molecules are at least 10, at least 15, at least 20, at least 30, at least 40, at least 50, and at least 70 nucleotides in length. In another embodiment, nucleic acid molecules that hybridize are of about the same length as the particular desired nucleic acid.

A "nucleic acid molecule" refers to the phosphate ester polymeric form of ribonucleosides (adenosine, guanosine, uridine, or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single-stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

As used herein, the term "homologs" refers to genes in different species that apparently evolved from a common ancestral gene by speciation and/or did not evolve through speciation but exhibit convergent evolution, which is encoding for a polypeptide that exhibits a similar activity or phenotype despite no significant similarity in their gene sequences. Normally, homologs that apparently evolved from a common ancestral gene by speciation exhibit the same function. Identification of homologs that apparently evolved from a common ancestral gene by speciation can provide reliable prediction of gene function in newly sequenced genomes. Sequence comparison algorithms that can be used to identify homologs that apparently evolved from a common ancestral gene by speciation include without limitation BLAST, FASTA, DNA Strider, and the GCG pileup program. Homologs often have high sequence similarity. In contrast, homologs that arose through convergent evolution display no significant sequence similarity, but exhibit similar activity or phenotype. TAP inhibitor activity can be determined by measuring the ability of the polypeptide to inhibit TAP-dependent transport of peptides into the endoplasmic reticulum of whole cells or subcellular fractions such as microsomes. The present invention encompasses all homologs of the desired polypeptide.

The terms "percent (%) sequence similarity", "percent (%) sequence identity", and the like, generally refer to the degree of identity or correspondence between different nucleotide sequences of nucleic acid molecules or amino acid sequences of polypeptides that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al, J. Mol. Biol. 1990; 215: 403. BLAST nucleotide searches can be performed with the NBLAST program, score=100, word length=12, to obtain nucleotide sequences homologous to sequences of the invention. BLAST protein searches can be performed with the XBLAST program, score=50, word length=3, to obtain amino acid sequences homologous to protein sequences of the invention. To obtain gapped alignments for comparison purposes, Gapped BLAST can be utilized as described in Altschul et al, Nucleic Acids Res. 1997, 25:3389. Alternatively, PSI-Blast can be used to perform an iterated search that detects distant relationship between molecules. See Altschul et al., (1997) supra. When utilizing BLAST, Gapped BLAST, and PSI-Blast programs, the default parameters of the respective programs (e.g., XBLAST and NBLAST) can be used. See ncbi.nlm nih.gov/BLAST/ on the World Wide Web.

Another non-limiting example of a mathematical algorithm utilized for the comparison of sequences is the algorithm of Myers and Miller, CABIOS 1988; 4: 1 1-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (J. Mol. Biol. 1970, 48:444-453), which has been incorporated into the GAP program in the GCG software package (Accelrys, Burlington, Mass.; available at accelrys.com on the World Wide Web), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

Statistical analysis of the properties described herein may be carried out by standard tests, for example, t-tests, ANOVA, or Chi squared tests. Typically, statistical significance will be measured to a level of p=0.05 (5%), more preferably p=0.01, p=0.001, p=0.0001, p=0.000001.

Assays Measuring Exogenous TAP Inhibitor Armed Oncolytic Viral Activity

The properties of the exogenous TAP inhibitor armed oncolytic virus with respect to tumor cells can be measured in any manner known in the art. For example, the capacity of a exogenous TAP inhibitor armed oncolytic virus to infect a tumor cell can be quantified by measuring the exogenous TAP inhibitor armed oncolytic virus' capacity to replicate in a tumor cell, as measured by growth measurements, e.g., by measuring virus growth (viral titer) in cells over a period of 6, 12, 24, 36, 48 or 72 hours or longer. The ability of a exogenous TAP inhibitor armed oncolytic virus to infect and replicate within a tumor cell can be measured by determining the percentage of cells exhibiting a cytopathic effect (cpe) following infection with the exogenous TAP inhibitor armed oncolytic virus, wherein a exogenous TAP inhibitor armed oncolytic virus having the ability to infect cells will induce a cpe in at least about 50%, 60%, 70%, 80% or preferably 90% of the cells. The ability of an exogenous TAP inhibitor armed oncolytic virus to infect and replicate within a tumor cell may also be measured indirectly by measuring production of viral polypeptides (e.g., by 35S cysteine and methionine labeling followed by SDS-PAGE and autoradiography and Western blot analysis).

The ability of a virus to kill tumor cells can be roughly quantitated by eye or more exactly quantitated by counting the number of live cells that remain over time for a given time point and multiplicity of infection (MOI) for given cell type. For example, comparisons may be made over 24, 48 or 72 hours and using any known tumor cell type. In particular, UMUC3 invasive, high-grade bladder cancer, HT29 colorectal adenocarcinoma, LNCaP.FGC prostate adenocarcinoma, MDA-MB-231 breast adenocarcinoma, SK-MEL-28 malignant melanoma or U-87 MG glioblastoma astrocytoma cells can be used. Other examples of cell lines that are well known in the art and which may be used include, but are not limited to, HTB-161, SW620, A2780S, COLO205, A2780DDP, CX-1, SW948, SKBR3, MCF-7, HCT-15, CACO-2, A549, NEC, LX-1, T47D, B7474, DU145, PC3, SK-MEL-303, and LN-CAP cell lines. Any one of these cell types or any combination of these cell types can be used, as may other tumor cell types. It may be desirable to construct a standard panel of tumor cell types for this purpose. To count the number of live cells remaining at a given time point, the number of trypan blue-excluding cells (i.e., live cells) can be counted.

Quantitation may also be carried out by fluorescence activated cell sorting (FACS) or MTT assay. Tumor cell-killing ability may also be measured in vivo, e.g., by measuring the reduction in tumor volume engendered by a particular virus, as described.

In order to determine the properties of exogenous TAP inhibitor armed oncolytic virus of the invention, it will generally be desirable to use a standard laboratory reference strain for comparison. Any suitable standard laboratory reference strain may be used. In the case of Vaccinia, it is preferred to use one or more of the following vaccinia strains: Wyeth, Lister, Temple of Heaven, Patwadanger, and Modified Vaccinia Virus Ankara. Preferred examples of adenovirus include, but are not limited to, Adenovirus serotypes 5, 2, and 3. The reference strain will typically have equivalent modifications to the strain of the invention being tested. Thus, the reference strain will typically have equivalent modifications, such as gene deletions and heterologous gene insertions. In the case of an exogenous TAP inhibitor armed oncolytic virus of the invention virulence or pathology causing genes will also have been rendered non-functional in the reference strain. The modifications made to the reference strain may be identical to those made to the strain of the invention. By this, it is meant that the gene disruptions in the reference strain will be in exactly equivalent positions to those in the strain of the invention (e.g., deletions will be of the same size and in the same place). Similarly, in these embodiments, heterologous genes will be inserted in the same place, driven by the same promoter, etc. However, it is not essential that identical modifications be made. What is important is that the reference strain has functionally equivalent modifications, e.g., that the same genes are rendered non-functional and/or the same heterologous gene or genes is inserted.

A number of biological assays are available to evaluate and to optimize the choice of exogenous TAP inhibitor armed oncolytic virus and compositions comprising exogenous TAP inhibitor armed oncolytic virus for optimal antitumor/anticancer activity. These assays can be roughly split into two groups; those involving in vitro exposure of exogenous TAP inhibitor armed oncolytic virus to tumor/cancer cells and in vivo antitumor/anticancer assays in rodent models and rarely, in larger animals.

Cytolytic assays in vitro for TAP inhibition activity generally involve the use of established tumor/cancer cell lines both of animal and of human origin. These cell lines can be obtained from commercial sources such as the American Type Tissue Culture Laboratory in Bethesda, Md., and from tumor/cancer cell banks at research institutions. Exposures to exogenous TAP inhibitor armed oncolytic virus may be carried out under simulated physiological conditions of temperature, oxygen and nutrient availability in the laboratory. The endpoints for these in vitro assays can involve: 1) colony formation; 2) a simple quantitation of cell division over time; 3) the uptake of so called "vital" dyes which are excluded from cells with an intact cytoplasmic membrane; 4) the incorporation of radiolabeled nutrients into a proliferating (viable) cell. Colony forming assays have been used both with established cell lines, as well as fresh tumor biopsies surgically removed from patients with cancer. In this type of assay, cells are typically grown in petri dishes on soft agar, and the number of colonies or groups of cells (>60 m in size) are counted either visually, or with an automated image analysis system. A comparison is then made to the untreated control cells allowed to develop colonies under identical conditions. Because colony formation is one of the hallmarks of the cancer phenotype, only malignant cells will form colonies without adherence to a solid matrix. This can therefore be used as a screening procedure and assay for effectiveness for exogenous TAP inhibitor armed oncolytic virus, and there are a number of publications which show that results obtained in colony forming assays correlate with clinical trial findings with the same drugs.

The enumeration of the total number of cells is one approach to in vitro testing with either cell lines or fresh tumor biopsies. In this assay, clumps of cells are typically disaggregated into single units which can then be counted either manually on a microscopic grid or using an automated flow system such as either flow cytometry or a Coulter™ counter. Control (untreated) cell growth rates are then compared to the treated (with a nucleic acid) cell growth rates. Vital dye staining is another one of the older hallmarks of antitumor assays. In this type of approach cells either untreated or treated with the exogenous TAP inhibitor armed oncolytic virus are subsequently exposed to a dye such as methylene blue, which is normally excluded from intact (viable) cells. The number of cells taking up the dye (dead or dying) is the numerator with a denominator being the number of cells which exclude the dye.

In addition to vital dye staining, viability can be assessed using the incorporation of radiolabeled nutrients and/or nucleotides. In tumor cell assays, a typical experiment involves the incorporation of either (3H) tritium- or 14C-labeled nucleotides such as thymidine. Control (untreated) cells are shown to take up a substantial amount of this normal DNA building block per unit time, and the rate of incorporation is compared to that in the drug treated cells. This is a rapid and easily quantifiable assay that has the additional advantage of working well for cells that may not form large (countable) colonies. Drawbacks include the use of radioisotopes which present handling and disposal concerns.

There are large banks of human and rodent tumor/cancer cell lines that are available for these types of assays. Examples of suitable cell lines include but are not limited to UMUC3, T24, J82 and EJ (MGH-U1), J82 (CO), RT4, RT112, TCCSuP and SCaBER cells, which are bladder cancer cell lines. However, cell lines from other types of cancers (e.g., HT29 colorectal adenocarcinoma, LNCaP, FGC prostate adenocarcinoma, MDA-MB-231 breast adenocarcinoma, SK-MEL-28 malignant melanoma or U-87 MG) are also suitable. Other examples of suitable melanoma cell lines include without limitation, A-375, HS-695T, IGR-1, MEL-CLS-1, MEL-CL2, MEL-CLS3, MEL-CLS-4, MEWO, MML01, NIS-G, SK-MEL-1, SK-MEL-2 and SK-MEL-5 (available, e.g., from Cell Line Services (Germany). Non-limiting examples of ovarian cancer cell lines, include, e.g., PA-1, Caov-3, SW 626 and SK-OV-3. Non-limiting examples of glioblastoma cell lines include, e.g., LN-18, U-87 MG, F98, T98G. Such cell lines are commercially available, e.g., from American Type Culture Collection (ATCC).

The current test system used by the National Cancer Institute uses a bank of over 60 established sensitive and multidrug-resistant human cell lines of a variety of cell subtypes. This typically involves 5-6 established and well-characterized human tumor/cancer cells of a particular subtype, such as non-small cell or small cell lung cancer, for testing new agents. Using a graphic analysis system called Compare™, the overall sensitivity in terms of dye uptake (either sulforhodamine B or MTT tetrazolium dye) is determined. The specific goal of this approach is to identify nucleic acids that are uniquely active in a single histologic subtype of human cancer. In addition, there are a few sublines of human cancer that demonstrate resistance to multiple agents and are known to, in some cases, express the multidrug resistance pump, p-glycoprotein. The endpoint for certain assays is the incorporation of a protein dye called sulforhodamine B (for adherent tumor cells) and the reduction of a tetrazolium (blue) dye in active mitochondrial enzymes (for non-adherent, freely-floating types of cells).

In vitro assays that measure TAP-dependent peptide transport into the endoplasmic reticulum in whole cells or subcellular fractions such as microsomes can be used to measure the ability of an exogenous TAP inhibitor armed oncolytic virus to inhibit TAP.

Once an exogenous TAP inhibitor armed oncolytic virus of the invention has demonstrated some degree of activity in vitro at inhibiting tumor/cancer cell growth and/or at killing tumor cells, such as colony formation or dye uptake, anti-tumor/anti-tumor efficacy experiments are performed in vivo. Rodent systems can be used for initial assays of anti-tumor activity since tumor growth rates and survival endpoints are well-defined, and since these animals generally reflect the same types of toxicity and drug metabolism patterns as in humans. For this work, syngeneic (same gene line) tumors are typically harvested from donor animals, disaggregated, counted and then injected back into syngeneic (same strain) host mice. The exogenous TAP inhibitor armed oncolytic virus are typically then injected at some later time point(s), preferably by in situ injection into the tumor site or systemically administered by injection into veins or arteries or administered to a non-tumor site. Tumor growth rates and/or survival are determined and compared to untreated controls. In these assays, growth rates are typically measured for tumors growing in the flank of the animal, wherein perpendicular diameters of tumor width are translated into an estimate of total tumor mass or volume. The time to reach a predetermined mass is then compared to the time required for equal tumor growth in the untreated control animals.

In some embodiments, significant findings generally involve a >25% increase in the time to reach the predetermined mass in the treated animals compared to the controls. In other embodiments, significant findings involve a >50% increase in the time to reach the predetermined mass in the treated animals compared to the controls. The significant findings are termed "tumor growth inhibition" or "anti-tumor response."

Human tumors have been successfully transplanted in a variety of immunologically deficient mouse models. A mouse called the nu/nu or "nude" mouse can be used to develop in vivo assays of human tumor growth. In nude mice, which are typically hairless and lack a functional thymus gland, human tumors (millions of cells) are typically injected in the flank and tumor growth occurs slowly thereafter. This visible development of a palpable tumor mass is called a "take". The exogenous TAP inhibitor armed oncolytic virus disclosed herein can be injected by some route (intravenous, intramuscular, subcutaneous, per os) into or distal to the tumor implant site, and growth rates are calculated by perpendicular measures of the widest tumor widths as described earlier. A number of human tumors are known to successfully "take" in the nude mouse model. An alternative mouse model for this work involves mice with a severe combined immunodeficiency disease (SCID), in which there is a defect in maturation of lymphocytes. Because of this, SCID mice do not produce functional B- and T-lymphocytes. However, these animals do have normal natural killer (NK) cell activity. Nonetheless, SCID mice will "take" a large number of human tumors. Tumor measurements and drug dosing are generally performed as above. Again, positive compounds in the SCID mouse model are those that inhibit tumor growth rate by >20-50% compared to the untreated control.

For in vivo studies, such as for a study for efficacy of an exogenous TAP inhibitor armed oncolytic virus of the invention for treating bladder cancer, an orthotopic mouse model can be used which closely mimics bladder cancer in humans. The major utility of orthotopic cancer models is that it allows treatment of a tumor within the bladder and intravesical instillation into the bladder to be evaluated as a mode of therapy. Orthotopic models using human tumor cells can be examined in athymic, immunocompromised mice, whereas syngenic murine tumors can be utilized in immune competent mice. Transgenic mice that spontaneously develop tumors in the bladder can also be used. Such models provide important data regarding how effective an exogenous TAP inhibitor armed oncolytic virus of the invention will be, e.g., in an immune-competent human subject, such as a cancer patient.

The most commonly used immune competent mouse model that can be used to evaluate the exogenous TAP inhibitor armed oncolytic virus provided herein for the treatment of melanoma utilizes mouse B16F10 cells implanted into C57Bl/6 mice either s.c. or into organs, such as the brain, in order to initiate tumor formation. The anti-tumor efficacy of the exogenous TAP inhibitor armed oncolytic virus is then evaluated by administration to the animal in any number of ways, including e.g., direct injection into the tumor, injection into the mouse vasculature for systemic delivery, or intradermal injection in an area outside the tumor site. Measurement of tumor size, overall animal survival compared to control animals bearing tumors, and induction of immune cells that recognize and kill B16F10 cells can be measured as indicators of therapeutic efficacy. The model described in detail in Zamarin D et al., Gene Ther 2009; 16:796-804, which employed B 16F10 cells to evaluate the in vivo efficacy of an oncolytic virus for the treatment of metastatic melanoma can be used to evaluate the in vivo properties of the exogenous TAP inhibitor armed oncolytic virus described herein. The mouse model and methods described in Toda M et al., Hum Gene Ther 1999; 10:385-93, which employs DBA/2 mice harboring bilateral s.c. mouse melanoma tumors derived from cultured M3 melanoma cells can also be used to test the exogenous TAP inhibitor armed oncolytic virus.

There are a number of mouse ovarian cancer cell lines that are can be used in immune competent mice to evaluate the efficacy of the exogenous TAP inhibitor armed oncolytic virus for the treatment of metastatic ovarian cancer. Some common mouse ovarian cancer cell lines are MOSEC cells, ID8-VEGF, and Defb29-VEGF [see, Chalikonda S et al., Cancer Gene Ther 2008; 15: 115-25; Benencia F et al., Cancer Biology & Therapy 2008; 7: 1 194-205; and Hung C F et al., Gene Ther 2007; 14:20-9]. Metastatic ovarian cancer usually presents as metastatic foci lining the peritoneal cavity. Therefore, most models involve intraperitoneal injection of cultured mouse ovarian cancer cells in order to establish metastatic ovarian cancer lesions lining the peritoneal cavity. The exogenous TAP inhibitor armed oncolytic virus described herein can then be instilled into the peritoneal cavity to facilitate infection of all tumors accessible to the virus. As with bladder and melanoma models, the exogenous TAP inhibitor armed oncolytic virus therapeutic efficacy can be measured by monitoring tumor size over time and overall animal survival compared to control animals bearing tumors, as well as induction of immune cells that recognize and kill the cancer cells.

4C8 and 203GL mouse glioblastoma cell lines can also be used in immune competent mice to evaluate the efficacy of the exogenous TAP inhibitor armed oncolytic virus for the treatment of glioblastoma [see, Heliums E K et al., Neuro-oncology 2005; 7:213-24; Markert J M et al., J Virol 2012; 86:5304-13; and Todo T et al., Hum Gene Ther 1999; 10:2741-55]. Mouse glioblastoma models typically, although not necessarily, employ orthotopic tumors established by drilling a burr hole through the mouse cranium, then injecting cultured mouse glioma cells into the frontal lobes and closing the wound with a suture. At a predetermined time point after intracranial tumor implantation, the burr holes are reopened and exogenous TAP inhibitor armed oncolytic virus is directly injected into the tumor. Overall animal survival compared to control animals bearing tumors can be used as a measure of the efficacy of the therapy, since tumor size can typically only be measured postmortem. Examples of murine models of glioma are described, e.g., in Bruggeman et al., 2007; Cancer Cell; 12(4):328-341; and Marumoto T et al., Nat Med. 2009 15(1): 1 10-6.

All of these test systems are generally combined in a serial order, moving from in vitro to in vivo, to characterize the anti-tumor activity of exogenous TAP inhibitor armed oncolytic virus of the invention. The initial experiments in animals generally involve toxicity testing to determine a tolerable dose schedule and then using that dose schedule, to evaluate anti-tumor efficacy as described above. Exogenous TAP inhibitor armed oncolytic virus from these two types of assays may then be tested in human tumors growing in SCID or nude mice and if activity is confirmed, these exogenous TAP inhibitor armed oncolytic virus then become candidates for potential clinical drug development.

Exogenous TAP Inhibitor Armed Oncolytic Virus Can Comprise Additional Gene Sequences Mutations may be made in the exogenous TAP inhibitor armed oncolytic virus by homologous recombination methods well known to those skilled in the art. For example, viral genomic DNA is transfected together with a vector, preferably a plasmid vector, comprising the mutated sequence flanked by homologous viral genomic sequences. The mutated sequence may comprise a deletion(s), insertion(s) or substitution(s), all of which may be constructed by routine techniques. Insertions may include selectable marker genes, for example lacZ or green fluorescent protein (GFP), which may be used for screening recombinant viruses, for example, β-galactosidase activity or fluorescence.

In a preferred embodiment, a heterologous polypeptide encoding a gene of interest may be inserted into the exogenous TAP inhibitor armed oncolytic virus by any suitable technique such as homologous recombination of vaccinia strains with, for example, plasmid vectors carrying the gene flanked by vaccinia sequences. For example, a gene encoding a heterologous polypeptide can be inserted into a gene expression cassette that is flanked by sequences homologous to the upstream and downstream regions of the vaccinia Tk locus such that the gene under expression control of the gene expression cassette is targeted to the Tk locus on the vaccinia virus. The heterologous polypeptide encoding gene may be fused to a vaccinia promoter in an expression cassette, for example the tk promoter or the early/late promoter 7.5k. In some embodiments, the exogenous TAP inhibitor armed oncolytic virus comprises two genes encoding heterologous polypeptides, wherein the expression of each gene may be driven by separate vaccinia promoters, e.g. tk, 7.5k, or the synthetic early/late promoters or any of these promoters in combination with eukaryotic promoters that utilize host cell RNA polymerase in the nucleus such as the CMV and EF1α promoters. Where both heterologous polypeptide encoding genes are expressed from a single promoter, the genes may be separated by an internal ribosome entry site (IRES). The genes may also be expressed as a translational fusion such that the fused polypeptide retains both activities of the separate genes (e.g., prodrug activation and cell to cell fusion, prodrug activation and immunomodulatory activity or cell to cell fusion and immunomodulatory activity) such that the fused polypeptides are cleaved following expression by a protease either in cis or in trans to the fused polypeptide. It is also possible that the fused polypeptides are not separated by a cleavage site but still retain the activities of the separate genes.

The transcribed sequences of the inserted genes are preferably operably associated with control sequences permitting expression of the genes in a tumor cell. A control sequence typically comprises a promoter allowing expression of the gene operably associated therewith and signal for termination of transcription. The promoter is selected from promoters which are functional in mammalian, preferably human tumor cells. The promoter may be derived from promoter sequences of a eukaryotic gene. For example, the promoter may be derived from the genome of a cell in which expression of the heterologous gene is to occur, preferably a mammalian tumor cell, more preferably a human tumor cell. With respect to eukaryotic promoters, they may be promoters that function in a ubiquitous manner (such as promoters of β-actin, tubulin) or, alternatively, in a tumor-specific manner. They may also be promoters that respond to specific stimuli, for example promoters that bind steroid hormone receptors. Viral promoters may also be used, for example the Moloney murine leukaemia virus long terminal repeat (MMLV LTR) promoter or other retroviral promoters such as that derived from Rous sarcoma virus (RSV), the human or mouse cytomegalovirus (CMV) IE promoter or promoters of herpes virus genes including those driving expression of the latency associated transcripts.

Expression cassettes and other suitable constructs comprising, for example, the prodrug converting enzyme encoding gene, gene encoding a polypeptide capable of promoting cell to cell fusion and/or immunomodulatory gene and control sequences can be made using routine cloning techniques known to persons skilled in the art (see, for example, Sambrook et al., 1989, Molecular Cloning—A laboratory manual; Cold Spring Harbor Press).

It may also be advantageous for the promoter(s) to be inducible so that the levels of expression of the genes can be regulated during the life-time of the tumor cell. Inducible means that the levels of expression obtained using the promoter can be regulated. For example, an exogenous TAP inhibitor armed oncolytic virus of the invention may further comprise a heterologous gene encoding the tet repressor/VP16 transcriptional activator fusion protein under the control of a strong promoter (e.g., the CMV IE promoter) and the prodrug converting, cell to cell fusion or immunomodulatory or other gene may be under the control of a promoter responsive to the tet repressor VP 16 transcriptional activator fusion protein previously reported (see, Gossen et al., "Tight control of gene expression in mammalian cells by tetracycline-responsive promoters," Proc. Natl. Acad. Sci. USA, 89: 5547-5551, 1992; Gossen et al., "Transcriptional activation by tetracyclines in mammalian cells," Science, 268: 1766-1769, 1995). Thus, in this example, expression of the gene(s) would depend on the presence or absence of tetracycline.

An exogenous TAP inhibitor armed oncolytic virus of the invention can also encode multiple heterologous genes (e.g., prodrug converting enzyme encoding genes, genes encoding a polypeptide capable of promoting cell to cell fusion and/or immunomodulatory genes). An exogenous TAP inhibitor armed oncolytic virus of the invention may comprise one or more additional genes, for example from 1, 2, 3, 4, and/or 5 additional genes. The additional gene(s) may be further copies of the heterologous polypeptide encoding gene(s). The additional gene(s) may encode, for example one or more different prodrug converting gene, one or more different fusiogenic gene and/or one or more different immunomodulatory gene and/or one or more matrix modifying enzymes. The additional gene(s) may encode other gene(s) intended to enhance the therapeutic effect.

More than one gene and associated control sequences could be introduced into an exogenous TAP inhibitor armed oncolytic virus either at a single site or at multiple sites in the virus genome. Alternatively pairs of promoters (the same or different promoters) facing in opposite orientations away from each other, each driving the expression of a gene may be used.

In certain embodiments, a gene encoding a heterologous polypeptide is a prodrug activating enzyme, a heterologous gene encoding a polypeptide capable of causing cell to cell fusion or a heterologous gene encoding an immunomodulatory polypeptide. In a preferred embodiment, the exogenous TAP inhibitor armed oncolytic virus comprises at least two (2) genes encoding heterologous polypeptides.

Although the invention is not limited by any particular theory or mechanism of action, the insertion of the gene for mammalian GM-CSF into the genome of the exogenous TAP inhibitor armed oncolytic virus of the invention can enhance anti-tumor responses both locally and at sites distant to where the exogenous TAP inhibitor armed oncolytic virus is injected by stimulating T-cell mediated immune responses. GM-CSF is the principal mediator of proliferation, maturation, and migration of dendritic cells, the most potent antigen presenting cells of the immune system. Dendritic cells display antigens on their surface in conjunction with class II major histocompatibility complex (MHC-II). Once presented on MHC class II molecules, the antigen can be recognized by helper CD4+ T-cells, which provide support for the development of B cells and cytolytic CD8+ T-cells. Expression of GM-CSF in the local tumor environment serves to achieve several biologic goals: (a) induces local inflammation, (b) enhances dendritic cell activity, and (c) increases HLA class II expression. Further, in certain embodiments, cytokines having similar activity as GM-CSF, as described above, are also contemplated for use in the present invention. Under such increased immune recruitment and activation conditions, immunomodulatory polypeptides that lead to enhanced immune recruitment and activation could be deleterious to viral infection and spread. For this reason, the enhanced immune evasion capabilities of the exogenous TAP inhibitor armed oncolytic virus of the invention are particularly important for promoting viral replication, spread and efficacy.

In other embodiments, using standard molecular and virological techniques, an oncolytic virus strain (e.g., BV-49.5) may be modified to create novel, cancer-specific exogenous TAP inhibitor armed oncolytic virus of the present invention. For example, exogenous TAP inhibitor armed oncolytic virus may be engineered according to the invention where PI-3-kinase signaling is constitutively activated, e.g., by deleting the virus-encoded Akt mimic Us3. Alternatively, a key viral surface glycoprotein may be altered, such that the virus preferentially enters cells within the urothelium. An exogenous TAP inhibitor armed oncolytic virus of the invention may have either one or both of these modifications, and their oncolytic activity may be evaluated in both cell culture and animal models well known in the art.

Pharmaceutical Compositions

Pharmaceutical compositions include the exogenous TAP inhibitor armed oncolytic virus as described herein and a pharmaceutically acceptable carrier, excipient, or diluent.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

When formulated in a pharmaceutical composition, the exogenous TAP inhibitor armed oncolytic virus as described herein can be admixed with a pharmaceutically acceptable carrier or excipient. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human.

The term "pharmaceutically acceptable derivative" as used herein means any pharmaceutically acceptable salt, solvate or prodrug, e.g., ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol. 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

While it is possible to use a composition provided by the present invention for therapy as is, it may be preferable to administer it in a pharmaceutical formulation, e.g., in admixture with a suitable pharmaceutical excipient, diluent, or carrier selected with regard to the intended route of administration and standard pharmaceutical practice. Accordingly, in one aspect, the present invention provides a pharmaceutical composition or formulation comprising the exogenous TAP inhibitor armed oncolytic virus as described herein, or a pharmaceutically acceptable derivative thereof, in association with a pharmaceutically acceptable excipient, diluent, and/or carrier. The excipient, diluent and/or carrier must be "acceptable" in the sense of being compatible with the other ingredients of the formulation and not deleterious to the recipient thereof.

The exogenous TAP inhibitor armed oncolytic virus as described herein can be formulated for administration in any convenient way for use in human or veterinary medicine.

For human therapy, the pharmaceutical compositions, including each of the active agents, will be prepared in accordance with good manufacturing process (GMP) standards, as set by the Food & Drug Administration (FDA). Quality assurance (QA) and quality control (QC) standards will include testing for purity and function and other standard measures.

A preferred delivery vehicle is any chemical entity that ensures delivery of an exogenous TAP inhibitor armed oncolytic virus to a tumor cell in a selective manner, achieves sufficient concentration of the exogenous TAP inhibitor armed oncolytic virus in the tumor cell. This can include, without limitation, standard pharmaceutical dosage forms for the delivery of a virus (e.g., solutions, suspensions, emulsions) with or without controlled release. Other dosage forms, e.g., solid dosage forms such as, but not limited to, crystals or beads may also be used.

Therapeutic Uses

In certain embodiments, the present invention provides methods for killing tumor cells in a subject and for treating cancers. Preferred examples of cancers that can be treated using the described exogenous TAP inhibitor armed oncolytic viruses include, but are not limited to, melanoma, head and neck, ovarian and breast cancer, glioblastoma, bladder cancer and/or renal cancer. In one embodiment, an oncolytic or other virus of the invention can be used in a "stand alone" or monotherapy to treat such cancers. However, the invention also includes methods and compositions where an oncolytic or other virus of the invention is combined with at least one other therapeutic substance or treatment modality for treating cancer. In a preferred embodiment, the other therapeutic substance is cisplatin. However, any chemical or other agent used to treat bladder or other cancers can be used. Non-limiting examples of cancers that can be treated using the exogenous TAP inhibitor armed oncolytic virus of the invention include, e.g., prostate cancer, glioma, melanoma, colon cancer, ovarian cancer, breast cancer, head/neck cancer, and including all solid tumors.

The specific conditions (e.g., appropriate pharmaceutical carrier, dosage, site and route of administration, etc.) under which an exogenous TAP inhibitor armed oncolytic virus-containing composition of the invention should be administered in order to be effective for killing tumor cells or for treating cancer is an individual can be determined, e.g., by the individual's physician.

Individuals that can be treated according to the methods described herein include mammals, such as humans, rodents, dogs, cats, etc.

The exogenous TAP inhibitor armed oncolytic virus of the invention may be used in a method of treating the human or animal body. In particular, exogenous TAP inhibitor armed oncolytic viruses of the invention may be used in methods of cancer therapy. Preferably, an exogenous TAP inhibitor armed oncolytic virus of the invention is used in the oncolytic treatment of cancer. Viruses of the invention may be used in the therapeutic treatment of any solid tumor in a mammal, preferably a human. For example, viruses of the invention may be administered to a subject with prostate, breast, lung, liver, renal cell, endometrial, bladder, colon or cervical carcinoma; adenocarcinoma; melanoma; lymphoma; glioma; sarcomas such as soft tissue and bone sarcomas; or cancer of the head and neck, and, preferably, bladder cancer.

The term "cancer" refers to all types of cancer, neoplasm or malignant tumors found in mammals, including leukemia, carcinomas and sarcomas. Exemplary cancers include cancer of the breast, brain, cervix, colon, head and neck, liver, kidney, lung, non-small cell lung, small cell lung cancer, melanoma, mesothelioma, ovary, uterine, cervix, gall bladder, sarcoma, stomach, uterus and medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, urinary bladder cancer, gastric cancer, gastrointestinal stromal tumor, pancreatic cancer, germ cell tumors, mast cell tumors, mastocytosis, testicular cancers, glioblastoma, malignant pancreatic insulanoma, malignant carcinoid, urinary bladder cancer, premalignant skin lesions, testicular cancer, lymphomas, thyroid cancer, neuroblastoma, retinoblastoma, astrocytomas, sarcoma, osteosarcoma, B cell lymphoma, T cell lymphoma, NK cell lymphoma, Hodgkin's lymphoma, non-Hodgkin's lymphoma, melanoma, basal cell carcinoma, skin cancer, myeloma, leukemia, acute myelocytic leukemia (AML), acute lymphocytic leukemia (ALL), myelodysplastic syndrome, chronic lymphocytic leukemia (CLL) and chronic myelogenous leukemia (CML), esophageal cancer, genitourinary tract cancer, malignant hypercalcemia, endometrial cancer, adrenal cortical cancer, neoplasms of the endocrine and exocrine pancreas, and prostate cancer.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniformi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

In certain embodiments, the compositions provided herein are useful for killing tumor cells selected from the group consisting of astrocytoma, oligodendroglioma, meningioma, neurofibroma, glioblastoma, ependymoma, schwannoma, neurofibrosarcoma, medulloblastoma, melanoma cells, pancreatic cancer cells, prostate carcinoma cells, breast cancer cells, lung cancer cells, colon cancer cells, hepatoma cells, mesothelioma and epidermoid carcinoma cells.

In one preferred embodiment, the cancer to be treated is bladder cancer. Bladder cancer (BC) is the fifth most common human malignancy and the second most common genitourinary tumor. Intensive surveillance with cystoscopies, urinary cytologies, and frequent tumor resections under anesthesia make BC the most costly malignancy to treat. Despite advances in intravesical and systemic chemotherapy, immunotherapy, and surgery, the efficacy of present treatment options remains limited and the response transient. Significant problems still remain in managing BC patients. Notably, failure rates for treating high-grade superficial and invasive BC remain unacceptably high. In addition, current treatments not only adversely affect patient morbidity, but also present a large economic burden. Newer, more effective therapies that both improve patient outcomes and are more cost-effective would fill a significant need.

Compositions for killing tumor cells and/or for treating cancer in a subject can be advantageously used in combination with other treatment modalities, including without limitation radiation, chemotherapy, thermotherapy, molecular targeted therapies, and surgery.

Preferred chemotherapeutic agents used in the methods described herein include without limitation, include, taxol, taxotere and other taxoids (e.g., as disclosed in U.S. Pat. Nos. 4,857,653; 4,814,470; 4,924,01 1, 5,290,957; 5,292, 921; 5,438,072; 5,587,493; European Patent No. EP 253 738; and PCT Publication Nos. WO 91/17976, WO 93/00928, WO 93/00929, and WO 96/01815), cisplatin, carboplatin, (and other platinum intercalating compounds), etoposide and etoposide phosphate, bleomycin, mitomycin C, CCNU, doxorubicin, daunorubicin, idarubicin, ifosfamide, methotrexate, mercaptopurine, thioguanine, hydroxyurea, cytarabine, cyclophosphamide, nitrosoureas, mitomycin, dacarbazine, procarbizine, campathecins, dactinomycin, plicamycin, mitoxantrone, asparaginase, vinblastine, vincristine, vinorelbine, paclitaxel, docetaxel, calicheamicin, and the like.

Typical radiation therapy that can be used in combination with the exogenous TAP inhibitor armed oncolytic virus described herein includes without limitation radiation at 1-2 Gy. Examples of radiation therapy include without limitation γ-radiation, neutron beam radiotherapy, electron beam radiotherapy, proton therapy, brachytherapy, and systemic radioactive isotopes.

Radiation therapy and chemotherapy via local delivery of radioconjugates and chemotherapeutics, may also be used in the methods described herein. Directing the cytotoxic exposure directly to the tumor itself is a commonly used approach to deliver a cytotoxic drug while minimizing the cytotoxic exposure of normal tissues. However, one of the factors which limit the effectiveness of such an approach is incomplete induction of tumor cell death because of limited dose delivery. Thus, it would be highly desirable to concurrently use an exogenous TAP inhibitor armed oncolytic virus to enhance the sensitivity of the tumor cells to the particular cytotoxic agent. Tumor-specific delivery is commonly achieved by conjugating a cytotoxic agent (e.g., a toxin (such as ricin) or a radioisotope) to an antibody that preferentially targets the tumor (e.g., glypican-3 in hepatocellular carcinoma, anti-CD2 in neuroblastoma, or anti-Her2-neu in certain breast carcinomas). The targeting may be also done with natural targeting (i.e., with radioactive iodine in the treatment of thyroid carcinoma), physical targeting (i.e., administration of a radioisotope to a particular body cavity), or other targeting polypeptide (e.g., ferritin in hepatocellular carcinoma).

In addition to combination with conventional cancer therapies such as chemotherapy, radiation therapy, thermotherapy, surgery (tumor resection), and TACE (trans arterial chemoembolization), the exogenous TAP inhibitor armed oncolytic vector therapy in tumor or cancer cells can be combined with other anti-tumor/anti-cancer therapies, including but by no means limited to small tyrosine kinase inhibitors (e.g., sorafenib, erlotinib, gefitinib, brivanib, sunitinib, lapatinib, cediranib, vatalanib), monoclonal antibodies (e.g., cetuximab, bevacizumab, IMC-A12, IMC1 121B, panirumumab, trastuzumab), suicide gene therapy (i.e., introduction of genes that encode enzymes capable of conferring to tumor cells sensitivity to chemotherapeutic agents such as thymidine kinase of herpes simplex virus or varicella zoster virus and bacterial cytosine deaminase), anti-oncogene or tumor suppressor gene therapy (e.g., using anti-oncogene molecules including monoclonal antibodies, single chain antibody vectors, antisense oligonucleotide constructs, ribozymes, immunogenic peptides, etc.), administration of tumor growth inhibitors (e.g., interferon (IFN)-γ, tumor necrosis factor (TNF)-a, TNF-β, and similar cytokines, antagonists of tumor growth factor (TGF)- and IL-10, etc.), administration of angiogenesis inhibitors (e.g., fragments of angiogenic polypeptides that are inhibitory [such as the ATF of urokinase], angiogenesis inhibitory factors [such as angiostatin and endostatin], tissue inhibitors of metalloproteinase, soluble receptors of angiogenic factors [such as the urokinase receptor or FGF/VEGF receptor], molecules which block endothelial cell growth factor receptors, and Tie-1 or Tie-2 inhibitors), vasoconstrictive agents (e.g., nitric oxide inhibitors), immune therapies with an immunologically active polypeptide (including immunostimulation, e.g., in which the active polypeptide is a cytokine, lymphokine, or chemokine [e.g., IL-2, GM-CSF, IL-12, IL-4], and vaccination, in which the active polypeptide is a tumor specific or tumor associated antigen), and any other small molecules useful for treating cancer including pro-apoptotic agents (e.g. mapatumumab), proteosome inhibitors (e.g., bortezomib), cell cycle inhibitors (e.g., flavopiridol), DNA methylation inhibitors (e.g., 5-Aza-cytidine) and the like.

Tumor load is assessed prior to therapy by means of objective scans of the tumor such as with x-ray radiographs, computerized tomography (CAT scans), nuclear magnetic resonance (NMR) scans or direct physical palpation of the tumor mass. Alternatively, the tumor may secrete a marker substance such as alpha-fetoprotein from colon cancer, CA 125 antigen from ovarian cancer, or serum myeloma "M" protein from multiple myeloma, or AFP for hepatocellular carcinoma. The levels of these secreted products then allow for an estimate of tumor burden to be calculated. These direct and indirect measures of the tumor load are done pre-therapy, and are then repeated at intervals following the administration of the drug in order to gauge whether or not an objective response has been obtained. An objective response in cancer therapy generally indicates >50% shrinkage of the measurable tumor disease (a partial response), or complete disappearance of all measurable disease (a complete response). Typically these responses must be maintained for a certain time period, usually one month, to be classified as a true partial or complete response. In addition, there may be stabilization of the rapid growth of a tumor or there may be tumor shrinkage that is <50%, termed a minor response or stable disease.

In general, increased survival is associated with obtaining a complete response to therapy and, in some cases, a partial response if maintained for prolonged periods can also contribute to enhanced survival in the patient. Patients receiving chemotherapy are also typically "staged" as to the extent of their disease before and following chemotherapy are then restaged to see if this disease extent has changed. In some situations the tumor may shrink sufficiently and if no metastases are present, then surgical excision may be possible after chemotherapy treatment where it was not possible beforehand due to the widespread disease. In this case the chemotherapy treatment with the novel pharmaceutical compositions of the invention is being used as an adjuvant to potentially curative surgery. In addition, patients may have individual lesions in the spine or elsewhere that produce symptomatic problems such as pain and these may need to have local radiotherapy applied. This may be done in addition to the continued use of the systemic pharmaceutical compositions.

Patients are assessed for toxicity with each course of administration of an exogenous TAP inhibitor armed oncolytic virus of the invention or composition comprising an exogenous TAP inhibitor armed oncolytic virus, typically looking at effects on liver function enzymes and renal function enzymes such as creatinine clearance or blood urea nitrogen ("BUN") as well as effects on the bone marrow, typically a suppression of granulocytes important for fighting infection and/or a suppression of platelets important for hemostasis or stopping blood flow. For such assessments, normal blood counts may be reached between 1-3 weeks after therapy. Recovery then ensues over the next 1-2 weeks. Based on the recovery of normal white blood counts, treatments may then be resumed.

Typically, complete and partial responses are associated with at least a 1-2 log reduction in the number of tumor cells (a 90-99% effective therapy), although smaller or larger reductions in tumor burden are also possible. Patients with advanced cancer will typically have >$10^9$ tumor cells at diagnosis, multiple treatments may be required in order to reduce tumor burden to a very low state and potentially obtain a cure of the disease.

At the end of a treatment cycle with a pharmaceutical formulation of the invention, which could comprise several weeks of continuous drug dosing, patients can be evaluated for response to therapy (complete and partial remissions), toxicity measured by blood work and general well-being classified performance status or quality of life analysis. The latter includes the general activity level of the patient and their ability to do normal daily functions. It has been found to be a strong predictor of response and some anti-cancer drugs may actually improve performance status and a general sense of well-being without causing significant tumor shrinkage. Thus, for some cancers that are not curable, the pharmaceutical formulations may similarly provide a significant benefit, well-being performance status, etc. without affecting true complete or partial remission of the disease.

Administration

The exogenous TAP inhibitor armed oncolytic virus of the invention or compositions, e.g., pharmaceutical compositions, comprising the exogenous TAP inhibitor armed oncolytic virus, may be administered to an individual, e.g., patient, preferably a human patient, in need of treatment. A subject or patient in need of treatment is an individual suffering from cancer, preferably an individual with a solid tumor, and preferably is one who would benefit by the administration of the exogenous TAP inhibitor armed oncolytic virus or pharmaceutical composition thereof. The aim of therapeutic treatment is to improve the condition of a patient. Typically, although not necessarily, therapeutic treatment using an exogenous TAP inhibitor armed oncolytic virus or pharmaceutical composition of the invention alleviates the symptoms of the cancer. A method of treatment of cancer according to the invention comprises administering a therapeutically effective amount of an exogenous TAP inhibitor armed oncolytic virus of the invention or of a pharmaceutical composition containing the exogenous TAP inhibitor armed oncolytic virus to a patient suffering from cancer. Administration of the exogenous TAP inhibitor armed oncolytic virus or composition of the invention to an individual suffering from a tumor will typically kill the cells of the tumor, thus decreasing the size of the tumor and/or reducing or preventing spread of malignant cells from the tumor.

An exogenous TAP inhibitor armed oncolytic virus or pharmaceutical composition thereof can be introduced parenterally, transmucosally, e.g., orally (per os), nasally, or rectally, or transdermally. Parental routes include intravenous, intra-arteriole, intra-muscular, intradermal, subcutaneous, intraperitoneal, intraventricular, and intracranial administration. For example, an exogenous TAP inhibitor armed oncolytic virus-containing composition can be administered by injection, infusion, instillation or inhalation. A preferred route of administration is by direct injection. For example, therapeutic treatment may be carried out following direct injection of the exogenous TAP inhibitor armed oncolytic virus composition into target tissue (i.e., "in situ administration"). The target tissue may be the tumor or a blood vessel supplying the tumor.

An exogenous TAP inhibitor armed oncolytic virus-containing compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

In addition to the formulations described previously, the exogenous TAP inhibitor armed oncolytic virus-containing compositions may also be formulated as a depot preparation. Such long acting formulations may be administered by implantation (for example subcutaneously or intramuscularly) or by intramuscular injection. Thus, for example, the exogenous TAP inhibitor armed oncolytic virus-containing compositions may be formulated with suitable polymeric or hydrophobic materials (for example, as an emulsion in an acceptable oil) or ion exchange resins, or as sparingly soluble derivatives, for example, as a sparingly soluble salt. In yet another embodiment, the therapeutic compound can be delivered in a controlled release system. For example, an exogenous TAP inhibitor armed oncolytic virus may be administered using intravenous infusion with a continuous pump, in a polymer matrix such as poly-lactic/glutamic acid (PLGA), a pellet containing a mixture of cholesterol and the active ingredient (Silastic R M.; Dow Corning, Midland, Mich.; see U.S. Pat. No. 5,554,601) implanted subcutaneously, an implantable osmotic pump, a transdermal patch, liposomes, or other modes of administration. In another embodiment, the active ingredient can be delivered in a vesicle, in particular a liposome (see Langer, Science 249: 1527-1533 (1990); Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

The routes of administration and dosages described are intended only as a guide since a skilled practitioner will be able to determine readily the optimum route of administration and dosage. The dosage may be determined according to various parameters, especially according to the location of the tumor, the size of the tumor, the age, weight and condition of the patient to be treated and the route of administration. Preferably the virus is administered by direct injection into the tumor. The virus may also be administered systemically or by injection into a blood vessel supplying the tumor. The optimum route of administration will depend on the location and size of the tumor.

Administration of the exogenous TAP inhibitor armed oncolytic virus-containing composition may be once a day, twice a day, or more often, but frequency may be decreased during a maintenance phase of the disease or disorder, e.g., once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the present compounds.

Keeping the above description in mind, the amount of the exogenous TAP inhibitor armed oncolytic virus administered can be in the range of from $10^4$ to $10^{10}$ pfu, preferably from $10^5$ to $10^8$ pfu, more preferably about $10^6$ to $10^9$ pfu. Typically 1-4 ml, such as 2 to 3 ml of a pharmaceutical composition consisting essentially of the virus and a pharmaceutically acceptable suitable carrier or diluent would be used for direct injection into an individual tumor. [See, Senzer et al., J Clin Oncol (2009) 27(34):5763-5771.] However for some oncolytic therapy applications larger volumes up to 10 ml may also be used, depending on the tumor type, tumor size and the inoculation site. Likewise, smaller volumes of less than 1 ml may also be used. Dosages and administration regimen can be adjusted depending on the age, sex and physical condition of the subject or patient as well as the benefit of the treatment and side effects in the patient or mammalian subject to be treated and the judgment of the physician, as is appreciated by those skilled in the art.

The present invention is described here by means of the following examples. However, the use of examples anywhere in the specification is illustrative of and in no way limits the scope and meaning of the invention or of any exemplified terms. Likewise, the invention is not limited to any particular embodiment described herein. Indeed, many modifications and variations to those skilled in the art upon reading this specification and can be made without departing from its spirit and scope. The invention is therefore to be limited only by the terms of the appended claims along with the full scope of equivalents to which the claims are entitled. The disclosures of all citations, including issued patents, published applications, and scientific articles, in the specification are expressly incorporated herein by reference in their entirety.

It is to be understood that numerical values of binding activities and other parameters reported in the examples, and throughout the entire specification, are approximate. Individual measurements of these parameters may vary, e.g., due to normal experimental error and/or depending on the specific conditions used.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D.N. Glover ed. 1985); Oligonucleotide Synthesis (M. J. Gait ed. 1984); Nucleic Acid Hybridization [B. D. Hames & S. J. Higgins eds (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al., (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 4 28-431 (1998); Ray and Nickoloff, BioTech. 13: 342-346 (1992); Wang et al, BioTech. 19: 556-559 (1995); Wang and Malcolm, BioTech. 26: 680-682 (1999); Xu and Gong, BioTech. 26: 639-641 (1999), U.S. Pat. Nos. 5,789, 166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nuc. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al, Meth. Molec. Biol. 67: 209-218.

EXAMPLES

Example 1—Construction of Exogenous TAP Inhibitor Armed Oncolytic Virus

The exogenous TAP constructs described herein comprise a viral backbone derived from a virus lacking an endogenous gene encoding a TAP inhibitor and a polynucleotide sequence encoding an exogenous TAP inhibitor.

For example, a TAP inhibitor, such as UL49.5 derived from bovine herpes virus, can be inserted into a viral backbone as described herein. TAP inhibitors block the display of viral peptides to anti-viral CD8+ CTL in cells infected with herpesviruses encoding TAP inhibitors. This is a common strategy among herpesviruses to promote viral spread by slowing recognition and killing of infected cells by anti-viral CD8+ CTL, although this selective advantage has surprisingly not been found (with the exception of one example) outside of the herpesvirus family. Bovine Herpes Virus (BHV) UL49.5 is preferred to be included in the exogenous TAP inhibitor armed oncolytic viruses as described herein as it inhibits both mouse and human TAP and therefore can be used effectively in mouse studies to reasonably predict activity in humans.

Specifically, the following constructs can be designed. For example, a vaccinia viral backbone encoding UL49.5 under control of a vaccinia virus promoter can be inserted into the viral thymidine kinase gene. Other variants may include additional deletions of other viral genes such as vaccinia growth factor wherein the UL49.5 gene as well as another immunomodulatory polypeptide, a prodrug converting enzyme, and/or a matrix degrading enzyme may be include in the viral genome. Further, additional design variants may encode UL49.5 as well as another immunomodulatory polypeptide, a prodrug converting enzyme, and/or a matrix degrading enzyme under control of a vaccinia virus promoter in loci other than the viral TK locus. Specific examples include the following constructs:

1. BV-VV-ΔTK::49.5-sE/L: The UL49.5 gene under control of the synthetic early/late promoter and inserted into the thymidine kinase locus of a vaccinia virus.
2. BV-VV-ΔTK::49.5-p7.5: The UL49.5 gene under control of the p7.5 early/late promoter and inserted into the thymidine kinase locus of a vaccinia virus.
3. BV-VV-ΔTK::49.5-sE/L-pCMV: The UL49.5 gene under control of the synthetic early/late promoter as well as the cytomegalovirus (CMV) immediate early promoter with or without the CMV promoter enhancer and inserted into the thymidine kinase locus of a vaccinia virus.
4. BV-VV-ΔTK::49.5-p7.5-pCMV: The UL49.5 gene under control of the p7.5 early/late promoter as well as the cytomegalovirus (CMV) immediate early promoter with or without the CMV promoter enhancer and inserted into the thymidine kinase locus of a vaccinia virus.
5. BV-VV-ΔTK::49.5-sE/L-pEF1α: The UL49.5 gene under control of the synthetic early/late promoter as well as the EF1α promoter and inserted into the thymidine kinase locus of a vaccinia virus.
6. BV-VV-ΔTK::49.5-p7.5-pEF1α: The UL49.5 gene under control of the p7.5 early/late promoter as well as the EF1α promoter and inserted into the thymidine kinase locus of a vaccinia virus.
7. BV-VV-ΔVGFΔTK::49.5-sE/L: The UL49.5 gene under control of the synthetic early/late promoter and inserted into the thymidine kinase locus of a vaccinia virus wherein the virus also encodes a null allele of the viral growth factor gene.
8. BV-VV-ΔVGFΔTK::49.5-p7.5: The UL49.5 gene under control of the p7.5 early/late promoter and inserted into the thymidine kinase locus of a vaccinia virus wherein the virus also encodes a null allele of the viral growth factor gene.
9. BV-VV-ΔVGFΔTK::49.5-sE/L-pCMV: The UL49.5 gene under control of the synthetic early/late promoter as well as the cytomegalovirus (CMV) immediate early promoter with or without the CMV promoter enhancer and inserted into the thymidine kinase locus of a vaccinia virus wherein the virus also encodes a null allele of the viral growth factor gene.
10. BV-VV-ΔVGFΔTK::49.5-p7.5-pCMV: The UL49.5 gene under control of the p7.5 early/late promoter as well as the cytomegalovirus (CMV) immediate early promoter with or without the CMV promoter enhancer and inserted into the thymidine kinase locus of a vaccinia virus wherein the virus also encodes a null allele of the viral growth factor gene.
11. BV-VV-ΔVGFΔTK::49.5-sE/L-pEF1α: The UL49.5 gene under control of the synthetic early/late promoter as well as the EF1α promoter and inserted into the thymidine kinase locus of a vaccinia virus wherein the virus also encodes a null allele of the viral growth factor gene.
12. BV-VV-ΔVGFΔTK::49.5-p7.5-pEF1α: The UL49.5 gene under control of the p7.5 early/late promoter as well as the EF1α promoter and inserted into the thymidine kinase locus of a vaccinia virus wherein the virus also encodes a null allele of the viral growth factor gene.
13. BV-VV-ΔTKΔVGF::49.5-sE/L: The UL49.5 gene under control of the synthetic early/late promoter and inserted into the viral growth factor locus of a vaccinia virus wherein the virus also encodes a null allele of the viral thymidine kinase gene.
14. BV-VV-ΔTKΔVGF::49.5-p7.5: The UL49.5 gene under control of the p7.5 early/late promoter and inserted into the viral growth factor locus of a vaccinia virus wherein the virus also encodes a null allele of the viral thymidine kinase gene.
15. BV-VV-ΔTKΔVGF::49.5-sE/L-pCMV: The UL49.5 gene under control of the synthetic early/late promoter as well as the cytomegalovirus (CMV) immediate early promoter with or without the CMV promoter enhancer and inserted into the viral growth factor locus of a vaccinia virus wherein the virus also encodes a null allele of the viral thymidine kinase gene.
16. BV-VV-ΔTKΔVGF::49.5-p7.5-pCMV: The UL49.5 gene under control of the p7.5 early/late promoter as well as the cytomegalovirus (CMV) immediate early promoter with or without the CMV promoter enhancer and inserted into the viral growth factor locus of a vaccinia virus wherein the virus also encodes a null allele of the viral thymidine kinase gene.
17. BV-VV-ΔTKΔVGF::49.5-sE/L-pEF1α: The UL49.5 gene under control of the synthetic early/late promoter as well as the EF1α promoter and inserted into the viral growth factor locus of a vaccinia virus wherein the virus also encodes a null allele of the viral thymidine kinase gene.
18. BV-VV-ΔTKΔVGF::49.5-p7.5-pEF1α: The UL49.5 gene under control of the p7.5 early/late promoter as well as the EF1α promoter and inserted into the viral growth factor locus of a vaccinia virus wherein the virus also encodes a null allele of the viral thymidine kinase gene.

Further variants of the above listed vaccinia viruses may be constructed that additionally encode another immunomodulatory polypeptide, a prodrug converting enzyme, and/or a matrix degrading enzyme under any of the promoters described above for driving expression of UL49.5 and inserted into the TK locus, the VGF locus or both.

The following are examples of adenoviruses encoding UL49.5:

1. BV-Ad-ΔE1A::UL49.5: The UL49.5 gene inserted into the E1A locus of the adenoviral genome and under control of the E1A promoter.
2. BV-Ad-ΔE1A::pCMV:UL49.5: The UL49.5 gene inserted into the E1A locus of the adenoviral genome and under control of the CMV immediate early promoter with or without the CMV promoter enhancer.
3. BV-Ad-ΔE3-19KΔE1A::UL49.5: The UL49.5 gene inserted into the E1A locus of the adenoviral genome and under control of the E1A promoter wherein the virus also encodes a null allele of the E3 19K gene.
4. BV-Ad-ΔE3-19KΔE1A::pCMV:UL49.5: The UL49.5 gene inserted into the E1A locus of the adenoviral genome and under control of the CMV immediate early promoter with or without the CMV promoter enhancer wherein the virus also encodes a null allele of the E3 19K gene.

Further variants of the above listed adenoviruses may be constructed that additionally encode another immunomodulatory polypeptide, a prodrug converting enzyme, and/or a matrix degrading enzyme in place of the E3-19K gene and under control of either the endogenous adenoviral E3 promoter or a heterologous promoter such as the CMV promoter or EF1α.

The following are examples of vesicular stomatitis virus encoding UL49.5:
1. BV-VSV-G:UL49.5:L: The UL49.5 gene encoded in the VSV genome between the viral G and L genes under control of VSV transcription start and stop signals.
2. BV-VSV-M:UL49.5:G: The UL49.5 gene encoded in the VSV genome between the viral M and G genes under control of VSV transcription start and stop signals.
3. BV-VSV-ΔM51-G:UL49.5:L: The UL49.5 gene encoded in the VSV genome between the viral G and L genes under control of VSV transcription start and stop signals wherein the methionine 51 of the viral M gene is deleted.
4. BV-VSV-ΔM51-M:UL49.5:G: The UL49.5 gene encoded in the VSV genome between the viral M and G genes under control of VSV transcription start and stop signals wherein the methionine 51 of the viral M gene is deleted.
5. BV-VSV-G:UL49.5:L/M:IFNβ:G: The UL49.5 gene encoded in the VSV genome between the viral G and L genes under control of VSV transcription start and stop signals wherein the virus also encodes the interferon beta gene between the viral M and G genes under control of VSV transcription start and stop signals.
6. BV-VSV-M:UL49.5:G/G:IFNβ:L: The UL49.5 gene encoded in the VSV genome between the viral M and G genes under control of VSV transcription start and stop signals wherein the virus also encodes the interferon beta gene between the viral G and L genes under control of VSV transcription start and stop signals.

Further variants of the above listed vesicular stomatitis viruses may be constructed that additionally encode another immunomodulatory polypeptide, a prodrug converting enzyme, and/or a matrix degrading enzyme. These functions are located between the viral G and L genes and under control of VSV transcription start and stop signals in viruses where the UL49.5 gene is located between the viral M and G genes or located between the viral M and G genes and under control of VSV transcription start and stop signals in viruses where the UL49.5 gene is located between the viral G and L genes.

Once these exogenous TAP inhibitor armed oncolytic viruses are constructed, their genetic structure is analyzed by Southern Blot to ensure that the vector architecture is as predicted and that the UL49.5 and/or other transgenes were correctly inserted. For example, viral DNA from high titer viral stocks derived from isolated plaques is prepared and digested with one, two, or more restriction enzymes that cut outside the inserted cassette and release fragments containing the ectopic transgenic sequences. Digested DNA is then separated on a 0.8% agarose gel, transferred to a nylon membrane and probed with a labeled fragment that hybridizes to the inserted cassette. Bands in each lane should agree with the predicted fragment sizes for each recombinant virus generated as well as the control viruses. In the case where the viral genome is composed of RNA, Northern blotting with probes that hybridize to the transgene cassette, a region outside the inserted transgene cassette, or both can be used to compare the genome of the recombinant to the parental virus as well as other control viruses and to verify that the actual genome size corresponds with the predicted size.

Comparison of viruses encoding UL49.5 to an isogenic UL49.5 frameshift mutant in immune competent mouse cancer models facilitates direct evaluation of the role TAP inhibition plays in oncolytic virus therapeutic efficacy. Furthermore, comparison of mice treated with viruses encoding UL49.5 to isogenic control viruses expressing another gene in place of UL49.5, e.g. GM-CSF, will determine the contribution UL49.5 makes to efficacy as compared to another gene, e.g. GM-CSF, a known and highly valued oncolytic virus armament.

Example 2—Confirmation of Viral Protein Synthesis and Viral Replication in Infected Cancer Cells To confirm that the exogenous TAP inhibitor armed oncolytic viruses described in Example 1 are able to promote viral protein synthesis in tumor cell lines, for example, human U373 glioblastoma cells and/or human bladder cancer cell lines (e.g., SCaBER or UMUC3) are either mock infected or infected with the exogenous TAP inhibitor armed oncolytic viruses described in Example 1 at MOI=5 for 2, 4, 6, 8, or 16 hrs. Rates of protein synthesis are then measured by adding radioactive amino acids to the media. Cell lysates are then prepared and polypeptides separated by SDS-PAGE followed by autoradiography to visualize the level of protein synthesis in each sample. It is expected that the pattern of protein synthesis should change in those exogenous TAP inhibitor armed oncolytic viruses as described above that have a high likelihood to be therapeutically effective due to viral use of the host protein synthesis apparatus for the manufacturing of viral polypeptides.

Sustained viral protein synthesis in the exogenous TAP inhibitor armed oncolytic viruses infected cells can often predict the level of viral yields as compared to WT. For example, but not limited to, U373 and UMUC3 cells as well as SCaBER cells, another aggressive human bladder cancer cell line, can be infected at low MOI (MOI=0.01) with either any of the exogenous TAP inhibitor armed oncolytic viruses described in Example 1. After three to five days, the cultures are processed and viral titers can be determined by plaque assay on Vero cells or other cells permissive for viral replication and virus titers can be measured and compared to WT titers.

Example 3—In Vitro TAP Inhibitory Activity of Non-HSV TAP Oncolytic Viruses

To confirm that the exogenous TAP inhibitor armed oncolytic viruses described in Example 1 are able to inhibit TAP, the steady state level of TAP in virally infected cells can be compared to cells infected with control viruses deficient in the UL49.5 TAP inhibitor by western blotting. A major mechanism UL49.5 employs to inhibit TAP is to direct proteasomal degradation of TAP. Therefore, the TAP inhibitory activity of UL49.5 can be measured by infecting cells with the exogenous TAP inhibitor armed oncolytic viruses described in Example 1 and comparing the steady state level of the polypeptides that form the TAP complex in these cells to cells infected with a control virus deficient in expression of UL49.5 polypeptide. Briefly, at various times post-infection, the infected cells are lysed by removing the culture media and adding Lemmli's Buffer. After vortexing the samples to shear cellular DNA and boiling the sample to denature proteins, polypeptides are then separated by SDS-PAGE, transferred to nylon or pvdf western blotting membranes and incubated with an antibody that binds a member of the TAP complex followed by addition of a HRP-conjugated secondary antibody for chemiluminscent detection of anti-TAP antibody bound polypeptides on the surface of the western blotting membrane. TAP inhibitory activity by UL49.5 is thus observed when the amount of a TAP complex protein in samples derived from cells infected with exogenous TAP inhibitor armed oncolytic viruses described in Example 1 is lower than cells infected with isogenic control viruses deficient in the UL49.5 polypeptide.

Additionally, TAP inhibitory activity in cells infected with the exogenous TAP inhibitor armed oncolytic viruses described in Example 1 is observed by downregulation of cell surface MHC-I complexes compared to cells infected with control viruses deficient in the TAP inhibitor. Cell surface MHC-I is detected by incubating infected cells with a fluorphore labeled antibody that binds MHC-I. Binding of the antibody can be detected by trypsinizing the cells if they are adherent, fixing them with 4% paraformaldehyde, and then analyzing them by flow cytometry to detect and quantify the amount of the fluorophore-labeled antibody bound on each cell.

Example 4—Animal Models for Tumor Eradication

The ability of an exogenous TAP inhibitor armed oncolytic virus described herein to eradicate human tumors can be tested in the following, well established animal model. Specifically, tumors are first established in BALB/c nu/nu mice by subcutaneous injection of SCaBER or UMUC3 human bladder cancer cells. Tumors are then harvested, cut into 2 mm$^3$ cubes and implanted subcutaneously into fresh BALB/c nu/nu mice. BALB/c nu/nu mice harboring established, subcutaneous SCaBER tumors measuring ≈50 mm$^3$ are injected on days 1, 3, 5, and 7 with 5×10$^6$ pfu with the exogenous TAP inhibitor armed oncolytic viruses described in Example 1 or a virus-free lysate prepared from mock-infected cells. Tumors are measured every 2 days for 43 days, after which the animals carrying vehicle treated tumors will be euthanized due to excessive tumor burden. The average normalized values reflecting relative tumor size on each day can then be plotted. The initial tumor volume immediately before treatment is normalized to a relative size of 1.0. Error bars can be used to reflect the SEM. Mice are considered cured if the tumors compared to vehicle treated tumors are substantially reduced.

In an alternative assay, mice are treated in a similar manner, but the animals in this experiment receive UMUC3 tumors and are injected with 5×10$^6$ pfu of the exogenous TAP inhibitor armed oncolytic viruses described in Example 1 on either days 1, 3, and 5. Control animals are injected with a virus-free lysate prepared from mock-infected cells. Animals carrying vehicle treated tumors will be euthanized due to excessive tumor burden after 11 days, whereas durable responses are measured in the treated animals. Positive results would demonstrate that the exogenous TAP inhibitor armed oncolytic viruses described herein promote viral replication and spread through human tumors, and thus may have therapeutic value in treating subjects.

Example 5—Therapeutic Oncolytic Virus Animal Studies

In proof of concept studies, the anti-tumor efficacy of the exogenous TAP inhibitor armed oncolytic viruses described, for example, in Example 1 can be compared to a genetically identical control virus into which a single frameshift mutation in the UL49.5 gene was inserted (FS Control). Using a bilateral subcutaneous tumor model (FIG. 1) two tumors are established at separate sites on, for example, but not limited to, a female C3H/HeN mouse (FIG. 1: Step 1) by injecting, for example, but not limited to, cultured MBT-2 cells, an aggressive mouse bladder carcinoma cell line. One tumor is implanted in the upper left quadrant while the other in the lower right flank. Once the tumors reach ~60 mm$^3$ (FIG. 1: Step 2), the exogenous TAP inhibitor armed oncolytic viruses described herein can be injected into the tumor on the left side (FIG. 1: Step 3). It is well established that many oncolytic viruses do not spread from the injected tumor to the contralateral tumor. Therefore, if the exogenous TAP inhibitor armed oncolytic virus treatment is unable to induce anti-tumor immunity, growth of the contralateral, uninjected tumor is unaffected (FIG. 1: Step 3a). However, if anti-tumor immunity is generated, growth of the contralateral tumor is retarded (FIG. 1: Step 3b).

Generally, ten days after MBT-2 injection (Day 0), tumors are measured to determine if they have reached ~60 mm$^3$ and three groups of animals are established such that the average tumor volumes on each flank are normalized between the groups. Also on Day 0, the untreated group is also given an intra-tumoral injection of 30 µl PBS into the left tumor. The other two groups receive 30 µl injections of exogenous TAP inhibitor armed oncolytic viruses described in Example 1 or isogenic FS control viruses or isogenic control viruses deficient in the exogenous TAP inhibitor function by a mechanism other than a frameshift mutation, such as, omission of the entire exogenous TAP inhibitor open reading frame. Second and third intra-tumoral injections of PBS or each virus are performed two-three days and five-six days after the first treatment, respectively. The length and width of each tumor is recorded at various times and tumor volume calculated using the formula $0.5 \times (L \times W^2)$.

Observation of a statistically significant difference in the volume of virally injected tumors compared to PBS controls would indicate that viruses replicate in the tumor microenvironment and slow tumor growth. Additionally, the relative ability of the exogenous TAP inhibitor armed oncolytic viruses described in Example 1 to induce anti-tumor immunity in the contra-lateral tumor can be measured by observing a statistically significant difference in the size of the contralateral tumors in the group treated with the exogenous TAP inhibitor armed oncolytic viruses described in Example 1 compared to the group treated with the isogenic FS control virus.

Additionally, the lymph nodes that drain the virus treated tumor or spleens from mice can be harvested on at least 3 days but less than 7 days after the last virus treatment and a cell population enriched for CD8+ cells obtained by positive or negative selection using Miltenyi CD8a (Ly-2) microbeads or the CD8a+ T-cell Isolation Kit and LS columns. Cells from this population are then added in triplicate to a mouse IFN-γ ELISPOT dish either alone (Media) or with mitomycin-C treated MBT-2 cells (MBT-2 Stimulated) and incubated at 37° C. for 40 hrs. The plates are then developed and the number of spot forming cells (SFC) in each well counted and the average for each animal calculated. Results are positive when cells obtained from the tumor draining lymph node or spleens of animals treated with the exogenous TAP inhibitor armed oncolytic viruses described herein secrete at least 3-fold higher average amount of IFN-γ in response to stimulation with MBT-2 cells compared to the average of animals from each other group. An in vitro finding of enhanced anti-tumor immune activity in animals treated with the exogenous TAP inhibitor armed oncolytic viruses would support the conclusion that TAP inhibition by the exogenous TAP inhibitor armed oncolytic viruses result in enhanced induction of anti-tumor immunity and therapeutic efficacy. In models where the tumor antigen is known, splenocytes, or EL4 cells in the case of C57Bl/6 mouse models, can be pulsed with the tumor antigen peptide and used in place of mitomycin-C treated tumor cells for measurement of IFN-γ release by CD8+ T-cells using ELISPOT. Finally, ELISAs can be used in place of ELISPOT assays to measure IFN-γ release by CD8+ T-cells.

To determine if UL49.5 promotes persistence of the exogenous TAP inhibitor armed oncolytic viruses in tumors, C3H/HeN mice with bilateral s.c. MBT-2 tumors are injected over 5 days with three doses of the exogenous TAP inhibitor armed oncolytic viruses described herein. At one-five days after the final injection, mice are sacrificed and tumors are weighed, minced, homogenized using Lysing Matrix D tubes (MP Biomedical) and bead beating, freeze-thawed three times, sonicated and viral titers determined by plaque assay on Vero cells or other cell lines permissive for replication and plaquing of the viruses.

Results are considered positive when there is an at least 3-fold higher average level of viral plaque forming units derived from tumors treated with the exogenous TAP inhibitor armed oncolytic viruses described in Example 1 compared to FS control.

What is claimed:

1. An exogenous TAP inhibitor armed oncolytic virus comprising:
   a. a viral backbone that in its wildtype form does not encode a TAP inhibitor, wherein said viral backbone is selected from Vaccinia virus, Adenovirus, Adeno-Associated virus, Myxoma virus, Vesicular Stomatitis virus, New Castle Disease virus, Seneca valley virus and Reovirus; and
   b. a polynucleotide sequence encoding a TAP inhibitor polypeptide sequence; and
   c. a polynucleotide sequence encoding an immunomodulatory polypeptide, wherein the immunomodulatory polypeptide is selected from:
      i. B7-1 (CD80);
      ii. B7-2 (CD86);
      iii. CD40L;
      iv. TNF-α;
      v. IL-10;
      vi. a PD-1 inhibitor;
      vii. a PDL-1 inhibitor;
      viii. a CTLA4 inhibitor;
      ix. CMV Us2;
      x. CMV Us11;
      xi. RANTES; or
      xii. MIP-3; and
   (d) a polynucleotide sequence encoding a prodrug converting enzyme and/or a matrix degrading enzyme.

2. The exogenous TAP inhibitor armed oncolytic virus of claim 1, wherein the TAP inhibitor polypeptide acid sequence is at least 70% identical to the amino acid sequence selected from:
   a. HSV-1 ICP47;
   b. Bovine herpes virus-1 UL49.5;
   c. Bubaline herpes virus-1 UL49.5;
   d. Cervid virus-1 UL49.5;
   e. Feline herpes virus-1 UL49.5;
   f. Equine herpes virus-1 UL49.5;
   g. Pseudorabies UL49.5;
   h. CMV US6;
   i. EBV BNLF2a; or
   j. CPXV CPXV12.

3. The exogenous TAP inhibitor armed oncolytic virus of claim 1, wherein the TAP inhibitor polypeptide acid sequence is at least 80%, 85%, 90%, 91%, 92%, 93%, 94%, 95%, 96%, 97%, 98%, or 99% identical to the amino acid sequence selected from:
   a. HSV-1 ICP47;
   b. Bovine herpes virus-1 UL49.5;
   c. Bubaline herpes virus-1 UL49.5;
   d. Cervid virus-1 UL49.5;
   e. Feline herpes virus-1 UL49.5;
   f. Equine herpes virus-1 UL49.5;
   g. Pseudorabies UL49.5;
   h. CMV US6;
   i. EBV BINLF2a; or
   j. CPXV CPXV12.

4. The exogenous TAP inhibitor armed oncolytic virus of claim 1, wherein the TAP inhibitor polypeptide sequence is selected from:
   a. HSV-1 ICP47;
   b. Bovine herpes virus-1 UL49.5;
   c. Bubaline herpes virus-1 UL49.5;
   d. Cervid virus-1 UL49.5;
   e. Feline herpes virus-1 UL49.5;
   f. Equine herpes virus-1 UL49.5;
   g. Pseudorabies UL49.5;
   h. CMV US6;
   i. EBV BINLF2a; or
   j. CPXV CPXV12.

5. The exogenous TAP inhibitor armed oncolytic virus of claim 1, wherein said prodrug converting enzyme is selected from:
   a. Cytosine deaminase;
   b. Uracil phosphoribosyltransferase; or
   c. Thymidine kinase.

6. The exogenous TAP inhibitor armed oncolytic virus of claim 1, wherein said matrix degrading enzyme is selected from:
   a. Collagenase;
   b. Gelatinase;
   c. Stromelysins;
   d. Relaxin;
   e. Bacterial collagenase; or
   f. Chondroitinase ABC I.

7. The exogenous TAP inhibitor armed oncolytic virus of claim 1, wherein said exogenous TAP inhibitor armed oncolytic virus further comprises a promoter selected from:
   a. a CMV promoter; or
   b. EFIα promoter.

8. A pharmaceutical composition comprising the exogenous TAP inhibitor armed oncolytic virus of claim 1.

9. The exogenous TAP inhibitor armed oncolytic virus of claim 1, wherein the immunomodulatory polypeptide is B7-1 (CD80).

10. The exogenous TAP inhibitor armed oncolytic virus of claim 1, wherein the immunomodulatory polypeptide is B7-2 (CD86).

11. The exogenous TAP inhibitor armed oncolytic virus of claim 1, wherein the immunomodulatory polypeptide is CD40L.

12. The exogenous TAP inhibitor armed oncolytic virus of claim 1, wherein the immunomodulatory polypeptide is TNF-α.

13. The exogenous TAP inhibitor armed oncolytic virus of claim 1, wherein the immunomodulatory polypeptide is IL-10.

14. The exogenous TAP inhibitor armed oncolytic virus of claim 1, wherein the immunomodulatory polypeptide is a PD-1 inhibitor.

15. The exogenous TAP inhibitor armed oncolytic virus of claim 1, wherein the immunomodulatory polypeptide is a PDL-1 inhibitor.

16. The exogenous TAP inhibitor armed oncolytic virus of claim 1, wherein the immunomodulatory polypeptide is a CTLA4 inhibitor.

17. The exogenous TAP inhibitor armed oncolytic virus of claim 1, wherein the immunomodulatory polypeptide is CMV Us2.

18. The exogenous TAP inhibitor armed oncolytic virus of claim 1, wherein the immunomodulatory polypeptide is CMV Us11.

19. The exogenous TAP inhibitor armed oncolytic virus of claim 1, wherein the immunomodulatory polypeptide is RANTES.

20. The exogenous TAP inhibitor armed oncolytic virus of claim 1, wherein the immunomodulatory polypeptide is MIP-3.

21. A method of treating a patient with cancer, wherein said method comprises administering to said patient a therapeutically effective amount of the exogenous TAP inhibitor armed oncolytic virus of claim 1.

22. The method of claim 21, wherein the exogenous TAP virus is administered prophylactically.

23. The method of claim 21, wherein said patient has cancer selected from:
a. melanoma;
b. head and neck cancer;
c. ovarian cancer;
d. breast cancer;
e. glioblastoma;
f. bladder cancer;
g. prostate cancer;
h. lung cancer;
i. liver cancer;
j. colorectal cancer;
k. pancreatic cancer; and
l. renal cancer.

* * * * *

UNITED STATES PATENT AND TRADEMARK OFFICE
CERTIFICATE OF CORRECTION

PATENT NO. : 10,232,003 B2
APPLICATION NO. : 15/129916
DATED : March 19, 2019
INVENTOR(S) : Matthew C. Mulvey, Steven Fuhrmann and Ram Aiyar Page 1 of 1

It is certified that error appears in the above-identified patent and that said Letters Patent is hereby corrected as shown below:

In the Claims

Column 39, Lines 45-50, should read:
--a viral backbone that in its wildtype form does not encode a TAP inhibitor, wherein said viral backbone is selected from Vaccinia virus, Adenovirus, Adeno-Associated virus, Myxoma virus, Vesicular Stomatitis virus, New Castle Disease virus, Seneca Valley virus and Reovirus; and--.

Column 40, Line 65, should read:
--EFIα promoter.--.

Signed and Sealed this
Tenth Day of March, 2020

Andrei Iancu
*Director of the United States Patent and Trademark Office*